United States Patent

Chapman, Jr. et al.

[11] Patent Number: 4,762,786
[45] Date of Patent: Aug. 9, 1988

[54] VECTORS AND CONDITIONS WHICH ALLOW GENETIC TRANSFORMATION OF CEPHALOSPORIUM

[75] Inventors: Jerry L. Chapman, Jr., Speedway; Thomas D. Ingolia, Indianapolis; Kevin R. Kaster; Stephen W. Queener, both of Indianapolis; Paul L. Skatrud, Greenwood, all of Ind.

[73] Assignee: Eli Lilly and Company, Indianapolis, Ind.

[21] Appl. No.: 654,919

[22] Filed: Sep. 27, 1984

[51] Int. Cl.⁴ .................. C12N 15/00; C12N 1/20; C12N 1/14; C12P 21/00
[52] U.S. Cl. .................. 435/172.3; 435/68; 435/70; 435/253; 435/254; 435/320; 435/886; 435/925; 435/926; 935/27; 935/28; 935/29; 935/56; 935/68; 935/75
[58] Field of Search .................. 435/172.3, 253, 254; 935/27, 28, 29

[56] References Cited

U.S. PATENT DOCUMENTS 4,492,758 1/1985 Esser et al. .................. 435/317
4,559,302 12/1985 Ingolia et al. .................. 435/172.3
4,615,974 10/1986 Kingsman et al. .................. 435/68

FOREIGN PATENT DOCUMENTS 82303155.4 1/1983 European Pat. Off. .

OTHER PUBLICATIONS

Chapman, J. L., et al., 1987, J. of Industrial Mirobiology, 27:165.
Jimenez, A. and Davies, J., 1980, Nature, 287: 869.
Hyman et al., 1982, Proc. Natl. Acad. Sci. U.S.A., 79: 1578.
Minuth et al., 1982, Current Genetics, 5: 227.
Tudzynski, P. and Esser, K., 1982, Current Genetics, 6: 153.
Stakrud, P. L. and Queener, S. W., 1984, Current Genetics, 8: 155.
Kaster, et al., 1984, Current Genetics, 8: 353.

Primary Examiner—Thomas G. Wiseman
Assistant Examiner—Thomas D. Mays
Attorney, Agent, or Firm—Gerald V. Dahling; Leroy Whitaker

[57] ABSTRACT

A method for transforming Cephalosporium and other lower eukaryotes is disclosed. The method involves inserting a recombinant DNA cloning vector comprising a *Saccharomyces cerevisiae* transcriptional and translational activating sequence positioned for expression of hygromycin phosphotransferase into a host cell and then growing the host cell under selective conditions. The vectors optionally further comprise Cephalosporium ribosomal DNA and also sequences that allow for replication and selection in *E. coli* and Streptomyces.

43 Claims, 8 Drawing Sheets

Restriction Site Map of
Plasmid pIT221
(8kb)

Restriction Site Map of
Plasmid pIT221
(8kb)

Restriction Site Map of
Plasmid pIT123
(5.7kb)

Restriction Site Map of
Plasmid pIT143
(3kb)

Restriction Site Map of
Plasmid pIT213
(10.8kb)

Restriction Site Map of
Plasmid pPS1
(7.5kb)

Restriction Site Map of Plasmid pIT220 (4.7kb)

Restriction Site Map of
Plasmid pIT219
(11kb)

Restriction Site Map of
Plasmid pPS6
(11.4kb)

VECTORS AND CONDITIONS WHICH ALLOW GENETIC TRANSFORMATION OF CEPHALOSPORIUM

SUMMARY OF THE INVENTION

The present invention is a genetic transformation system which provides a means for genetically transforming cephalosporin-producing fungi. *Cephalosporium acremonium* is presently employed in manufacturing facilities throughout the world to produce cephalosporin C, an intermediate used in the manufacture of clinically important cephem antibiotics. The genetic transformation system consists of a set of transformation conditions and recombinant DNA cloning vectors that allow uptake and expression of genes in *C. acremonium* and related taxa. As a result of such introduction, Cephalosporium transformants with new genotypes—present in the transformants but absent in the untransformed parent—are produced.

Heretofore, the development and exploitation of recombinant DNA technology have been retarded and made especially difficult in Cephalosporium and allied taxa because of the lack of recombinant DNA cloning vectors and transformation methods. In fact, prior to the present invention, Cephalosporium host cells had not been successfully transformed or manipulated using recombinant DNA techniques. The vectors and method of the present invention are applicable to Cephalosporium generally and thus represent a significant advance in the technical art.

The vectors of the present invention are particularly useful because they are relatively small, versatile and can be transformed and selected in any Cephalosporium cell that is sensitive to an antibiotic for which resistance is conferred. Since many of the clinically important cephalosporin antibiotics are produced from the *Cephalosporium acremonium* metabolite, cephalosporin C, it is desirable to develop cloning methods and vectors that are applicable to that industrially important organism. The present invention provides methods and vectors which allow for the cloning of entire groups of genes into Cephalosporium species both for increasing yields of known antibiotics as well as for producing new antibiotics and antibiotic derivatives.

The present invention not only provides vectors and methods for cloning DNA into Cephalosporium host cells but also provides for the convenient selection of transformants. Since transformation is a very low frequency event, such a functional test is a practical necessity for determining which cell(s), of among the millions of cells, has acquired the vector DNA. This is important because DNA sequences that are non-selectable can be inserted into the vectors and, upon transformation, cells containing the DNA can be isolated by appropriate selection techniques.

For purposes of the present invention, as disclosed and claimed herein, the following terms are as defined below.

Recombinant DNA Cloning Vector—any agent capable of genomic integration or autonomous replication, including, but not limited to plasmids, comprising a DNA molecule to which one or more additional DNA segments can be added.

Transformation—the introduction of DNA into a recipient host cell.

Transformant—a recipient host cell that has undergone transformation.

Restriction Fragment—any linear DNA generated by the action of one or more restriction enzymes.

Transcriptional Activating Sequence—a DNA sequence that codes for the transcription of DNA into messenger RNA (mRNA).

Translational Activating Sequence—a DNA sequence that codes for the translation of mRNA into a polypeptide.

Functional Polypeptide—a recoverable bioactive entirely heterologous or homologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bioinactivating homologous polypeptide which can be specifically cleaved.

Fused Gene Product—a recoverable heterologous polypeptide which is fused with a protein or whole of a homologous polypeptide.

Host Cell—a cell, including the viable protoplasts thereof, which is capable of being transformed.

DETAILED DESCRIPTION OF THE INVENTION

Figure 1:
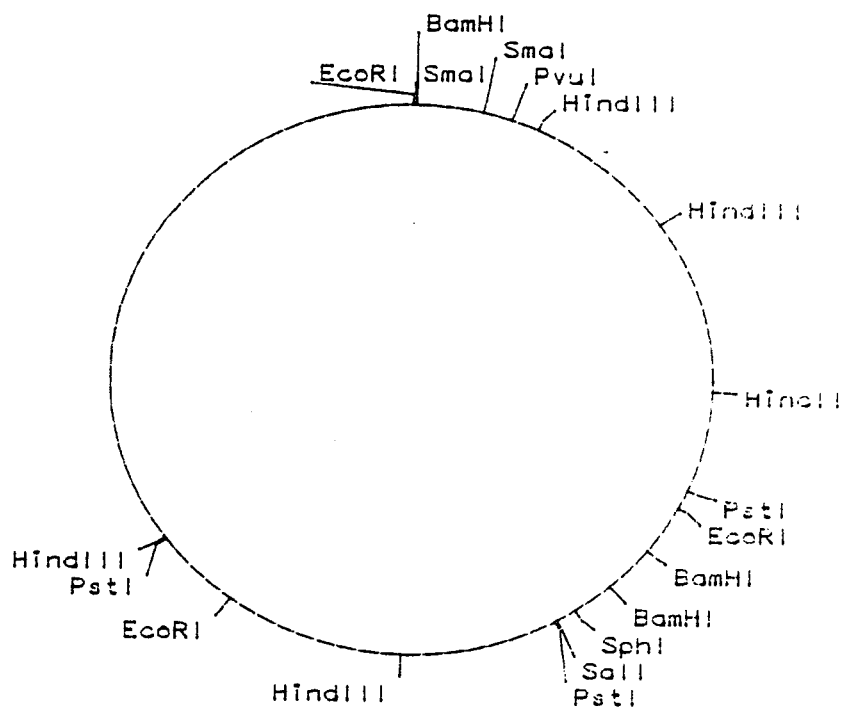
FIG. 1—Restriction Site Map of Plasmid pIT221.

The present invention is a method for transforming a Cephalosporium host cell which comprises (1) introducing a recombinant DNA cloning vector into a Cephalosporium host cell, said vector comprising
  (a) a *Saccharomyces cerevisiae* transcriptional and translational activating sequence positioned for expression of a sequence that codes for hygromycin B phosphotransferase and
  (b) a Cephalosporium-functional autonomous replication sequence, and (2) growing said host cell under selective conditions suitable for maintaining DNA comprising said vector in said host cell.

The invention further comprises the above-defined method wherein the recombinant cloning vector further comprises one or more of (1) an *E. coli* origin of replication and a sequence that codes for a selectable phenotype in *E. coli*,
(2) a Cephalosporium ribosomal gene sequence,
(3) a transcriptional and translational activating sequence positioned for expression of a sequence that codes for a functional polypeptide in Cephalosporium and (4) a Streptomyces origin of replication and a sequence that codes for a selectable phenotype in Streptomyces.

The invention also comprises the aforementioned recombinant DNA cloning vectors and related transformants employed to practice the method disclosed herein.

The present invention allows for the genetic transformation of Cephalosporium cells such that transformants with new genotypes are produced. These transformants are produced as a result of the introduction of vector-containing DNA sequences that code for polypeptides, regulatory DNA molecules or structural ribonucleic acid molecules. The present method, vectors and transformation conditions are especially useful for cloning and expressing natural or altered forms of foreign and Cephalosporium DNA. Altered forms of such sequences can be obtained by in vitro modification of the cloned natural sequences by standard recombinant DNA techniques.

The vectors used to practice the present transformation method each comprise a sequence that codes for a selectable marker in Cephalosporium. A preferred sequence, specified herein for illustrative purposes, codes for hygromycin B phosphotransferase and has the formula $$
\begin{array}{c}
R_m \\
| \\
R^1_m \\
LYS
\end{array}
$$

| $R^2_n$<br>\|<br>$R^3_n$ | CCT<br>\|\|\|<br>GGA<br>LYS | GAA<br>\|\|\|<br>CTT<br>PRO | CTC<br>\|\|\|<br>GAG<br>GLU | ACC<br>\|\|\|<br>TGG<br>LEU | GCG<br>\|\|\|<br>CGC<br>THR | ACG<br>\|\|\|<br>TGC<br>ALA | TCT<br>\|\|\|<br>AGA<br>THR | GTC<br>\|\|\|<br>CAG<br>SER | GAG<br>\|\|\|<br>CTC<br>VAL | AAG<br>\|\|\|<br>TTC<br>GLU | TTT<br>\|\|\|<br>AAA<br>LYS | CTG<br>\|\|\|<br>GAC<br>PHE | LEU |

| ATC | GAA | AAG | TTC | GAC | AGC | GTC | TCC | GAC | CTG | ATG | CAG | CTC |
| \|\|\| | \|\|\| | \|\|\| | \|\|\| | \|\|\| | \|\|\| | \|\|\| | \|\|\| | \|\|\| | \|\|\| | \|\|\| | \|\|\| | \|\|\| |
| TAG | CTT | TTC | AAG | CTG | TCG | CAG | AGG | CTG | GAC | TAC | GTC | GAG |
| ILE | GLU | LYS | PHE | ASP | SER | VAL | SER | ASP | LEU | MET | GLN | LEU |

| TCG | GAG | GGC | GAA | GAA | TCT | CGT | GCT | TTC | AGC | TTC | GAT | GTA |
| \|\|\| | \|\|\| | \|\|\| | \|\|\| | \|\|\| | \|\|\| | \|\|\| | \|\|\| | \|\|\| | \|\|\| | \|\|\| | \|\|\| | \|\|\| |
| AGC | CTC | CCG | CTT | CTT | AGA | GCA | CGA | AAG | TCG | AAG | CTA | CAT |
| SER | GLU | GLY | GLU | GLU | SER | ARG | ALA | PHE | SER | PHE | ASP | VAL |

| GGA | GGG | CGT | GGA | TAT | GTC | CTG | CGG | GTA | AAT | AGC | TGC | GCC |
| \|\|\| | \|\|\| | \|\|\| | \|\|\| | \|\|\| | \|\|\| | \|\|\| | \|\|\| | \|\|\| | \|\|\| | \|\|\| | \|\|\| | \|\|\| |
| CCT | CCC | GCA | CCT | ATA | CAG | GAC | GCC | CAT | TTA | TCG | ACG | CGG |
| GLY | GLY | ARG | GLY | TYR | VAL | LEU | ARG | VAL | ASN | SER | CYS | ALA |

| GAT | GGT | TTC | TAC | AAA | GAT | CGT | TAT | GTT | TAT | CGG | CAC | TTT |
| \|\|\| | \|\|\| | \|\|\| | \|\|\| | \|\|\| | \|\|\| | \|\|\| | \|\|\| | \|\|\| | \|\|\| | \|\|\| | \|\|\| | \|\|\| |
| CTA | CCA | AAG | ATG | TTT | CTA | GCA | ATA | CAA | ATA | GCC | GTG | AAA |
| ASP | GLY | PHE | TYR | LYS | ASP | ARG | TYR | VAL | TYR | ARG | HIS | PHE |

| GCA | TCG | GCC | GCG | CTC | CCG | ATT | CCG | GAA | GTG | CTT | GAC | ATT |
| \|\|\| | \|\|\| | \|\|\| | \|\|\| | \|\|\| | \|\|\| | \|\|\| | \|\|\| | \|\|\| | \|\|\| | \|\|\| | \|\|\| | \|\|\| |
| CGT | AGC | CGG | CGC | GAG | GGC | TAA | GGC | CTT | CAC | GAA | CTG | TAA |
| ALA | SER | ALA | ALA | LEU | PRO | ILE | PRO | GLU | VAL | LEU | ASP | ILE |

| GGG | GAA | TTC | AGC | GAG | AGC | CTG | ACC | TAT | TGC | ATC | TCC | CGC |
| \|\|\| | \|\|\| | \|\|\| | \|\|\| | \|\|\| | \|\|\| | \|\|\| | \|\|\| | \|\|\| | \|\|\| | \|\|\| | \|\|\| | \|\|\| |
| CCC | CTT | AAG | TCG | CTC | TCG | GAC | TGG | ATA | ACG | TAG | AGG | GCG |
| GLY | GLU | PHE | SER | GLU | SER | LEU | THR | TYR | CYS | ILE | SER | ARG |

| CGT | GCA | CAG | GGT | GTC | ACG | TTG | CAA | GAC | CTG | CCT | GAA | ACC |
| \|\|\| | \|\|\| | \|\|\| | \|\|\| | \|\|\| | \|\|\| | \|\|\| | \|\|\| | \|\|\| | \|\|\| | \|\|\| | \|\|\| | \|\|\| |
| GCA | CGT | GTC | CCA | CAG | TGC | AAC | GTT | CTG | GAC | GGA | CTT | TGG |
| ARG | ALA | GLN | GLY | VAL | THR | LEU | GLN | ASP | LEU | PRO | GLU | THR |

| GAA | CTG | CCC | GCT | GTT | CTG | CAG | CCG | GTC | GCG | GAG | GCC | ATG |
| \|\|\| | \|\|\| | \|\|\| | \|\|\| | \|\|\| | \|\|\| | \|\|\| | \|\|\| | \|\|\| | \|\|\| | \|\|\| | \|\|\| | \|\|\| |
| CTT | GAC | GGG | CGA | CAA | GAC | GTC | GGC | CAG | CGC | CTC | CGG | TAC |
| GLU | LEU | PRO | ALA | VAL | LEU | GLN | PRO | VAL | ALA | GLU | ALA | MET |

| GAT | GCG | ATC | GCT | GCG | GCC | GAT | CTT | AGC | CAG | ACG | AGC | GGG |
| \|\|\| | \|\|\| | \|\|\| | \|\|\| | \|\|\| | \|\|\| | \|\|\| | \|\|\| | \|\|\| | \|\|\| | \|\|\| | \|\|\| | \|\|\| |
| CTA | CGC | TAG | CGA | CGC | CGG | CTA | GAA | TCG | GTC | TGC | TCG | CCC |
| ASP | ALA | ILE | ALA | ALA | ALA | ASP | LEU | SER | GLN | THR | SER | GLY |

```
TTC GGC CCA TTC GGA CCG CAA GGA ATC GGT CAA TAC ACT
 |   |   |   |   |   |   |   |   |   |   |   |   |
AAG CCG GGT AAG CCT GGC GTT CCT TAG CCA GTT ATG TGA
PHE GLY PRO PHE GLY PRO GLN GLY ILE GLY GLN TYR THR

ACA TGG CGT GAT TTC ATA TGC GCG ATT GCT GAT CCC CAT
 |   |   |   |   |   |   |   |   |   |   |   |   |
TGT ACC GCA CTA AAG TAT ACG CGC TAA CGA CTA GGG GTA
THR TRP ARG ASP PHE ILE CYS ALA ILE ALA ASP PRO HIS

GTG TAT CAC TGG CAA ACT GTG ATG GAC GAC ACC GTC AGT
 |   |   |   |   |   |   |   |   |   |   |   |   |
CAC ATA GTG ACC GTT TGA CAC TAC CTG CTG TGG CAG TCA
VAL TYR HIS TRP GLN THR VAL MET ASP ASP THR VAL SER

GCG TCC GTC GCG CAG GCT CTC GAT GAG CTG ATG CTT TGG
 |   |   |   |   |   |   |   |   |   |   |   |   |
CGC AGG CAG CGC GTC CGA GAG CTA CTC GAC TAC GAA ACC
ALA SER VAL ALA GLN ALA LEU ASP GLU LEU MET LEU TRP

GCC GAG GAC TGC CCC GAA GTC CGG CAC CTC GTG CAC GCG
 |   |   |   |   |   |   |   |   |   |   |   |   |
CGG CTC CTG ACG GGG CTT CAG GCC GT  GAG CAC GTG CGC
ALA GLU ASP CYS PRO GLU VAL ARG HIS LEU VAL HIS ALA

GAT TTC GGC TCC AAC AAT GTC CTG ACG GAC AAT GGC CGC
 |   |   |   |   |   |   |   |   |   |   |   |   |
CTA AAG CCG AGG TTG TTA CAG GAC TGC CTG TTA CCG GCG
ASP PHE GLY SER ASN ASN VAL LEU THR ASP ASN GLY ARG

ATA ACA GCG GTC ATT GAC TGG AGC GAG GCG ATG TTC GGG
 |   |   |   |   |   |   |   |   |   |   |   |   |
TAT TGT CGC CAG TAA CTG ACC TCG CTC CGC TAC AAG CCC
ILE THR ALA VAL ILE ASP TRP SER GLU ALA MET PHE GLY

GAT TCC CAA TAC GAG GTC GCC AAC ATC TTC TTC TGG AGG
 |   |   |   |   |   |   |   |   |   |   |   |   |
CTA AGG GTT ATG CTC CAG CGG TTG TAG AAG AAG ACC TCC
ASP SER GLN TYR GLU VAL ALA ASN ILE PHE PHE TRP ARG

CCG TGG TTG GCT TGT ATG GAG CAG CAG ACG CGC TAC TTC
 |   |   |   |   |   |   |   |   |   |   |   |   |
GGC ACC AAC CGA ACA TAC CTC GTC GTC TGC GCG ATG AAG
PRO TRP LEU ALA CYS MET GLU GLN GLN THR ARG TYR PHE

GAT TTC GGC TCC AAC AAT GTC CTG ACG GAC AAT GGT CGC
 |   |   |   |   |   |   |   |   |   |   |   |   |
CTA AAG CCG AGG TTG TTA CAG GAC TGC CTG TTA CCG GCG
GLU ARG ARG HIS PRO GLU LEU ALA GLY SER PRO ARG LEU

ATA ACA GCG GTC ATT CAG RGG AGC CTC GCG ATG TTC GGG
 |   |   |   |   |   |   |   |   |   |   |   |   |
TAT TGT CGC CAG TAA CTG ACC TCG GAG CGC TAC AAG CCC
ARG ALA TYR MET LEU ARG ILE GLY LEU ASP GLN LEU TYR

GAT TCC CAA TAC GAG GTC GCC AAC ATC TTC TTC TGG AGG
 |   |   |   |   |   |   |   |   |   |   |   |   |
CTA AGG GTT ATG CTC CAG CGG TTG TAG AAG AAG ACC TCC
GLN SER LEU VAL ASP GLY ASN PHE ASP ASP ALA ALA TRP

CCG TGG TTG GCT TGT ATG GAG CAG CAG ACG CGC TAC TTC
 |   |   |   |   |   |   |   |   |   |   |   |   |
GGC ACC AAC CGA ACA TAC CTC GTC GTC TGC GCG ATG AAG
ALA GLN GLY ARG CYS ASP ALA ILE VAL ARG SER GLY ALA

GGG ACT GTC GGG CGT ACA CAA ATC GCC CGC AGC AGC GCG
 |   |   |   |   |   |   |   |   |   |   |   |   |
CCC TGA CAG CCC GCA TGT GTT TAG CGG GCG TCG TCG CGC
```

| | | | | | | | | | | | |
|---|---|---|---|---|---|---|---|---|---|---|---|
| GLY | THR | VAL | GLY | ARG | THR | GLN | ILE | ALA | ARG | ARG | SER | ALA |

-continued

```
GCC  GTC  TGG  ACC  GAT  GGC  TGT  GTA  GAA  GTA  CTC  GCC  GAT
|||  |||  |||  |||  |||  |||  |||  |||  |||  |||  |||  |||  |||
CGG  CAG  ACC  TGG  CTA  CCG  ACA  CAT  CTT  CAT  GAG  CGG  CTA
ALA  VAL  TRP  THR  ASP  GLY  CYS  VAL  GLU  VAL  LEU  ALA  ASP

AGT  GGA  AAC  CGA  CGC  CCC  AGC  ACT  CGT  CCG  AGG  GCA  AAG
|||  |||  |||  |||  |||  |||  |||  |||  |||  |||  |||  |||  |||
TCA  CCT  TTG  GCT  GCG  GGG  TCG  TGA  GCA  GGC  TCC  CGT  TTC
SER  GLY  ASN  ARG  ARG  PRO  SER  THR  ARG  PRO  ARG  ALA  LYS

GAA   R⁴
|||   |
CTT   R⁵
GLU
``` wherein
A is deoxyadenyl,
G is deoxyguanyl,
C is deoxycytidyl,
T is thymidyl,
R and $R^2$ are deoxyribonucleotide triplets that independently encode lysine,
$R^1$ and $R^3$ are deoxyribonucleotide triplets wherein the nitrogenous bases are complementary to the respective and corresponding bases of R and $R^2$,
m and n=0 or 1, subject to the limitation that when n=0, then m=0 and when m=1, then n=1,
$R^4$ is a deoxyribonucleotide triplet that encodes a translational stop codon and
$R^5$ is a deoxyribonucleotide triplet wherein the nitrogenous bases are complementary to the corresponding bases of $R^4$.
The amino acids encoded by the above DNA are designated below the appropriate nucleotide triplet. Accordingly,
MET is methionine,
LYS is lysine,
PRO is proline,
GLU is glutamic acid,
LEU is leucine,
THR is threonine,
ALA is alanine,
SER is serine,
VAL is valine,
PHE is phenylalanine,
ILE is isoleucine,
GLY is glycine,
ASP is aspartic acid,
GLN is glutamine,
ARG is arginine,
CYS is cysteine,
TRP is tryptophan,
ASN is asparagine,
HIS is histidine and
TYR is tyrosine.

The above sequence, of which R, $R^1$, $R^2$, $R^3$, $R^4$ and $R^5$ are defined in accordance with the genetic code (Watson, J. D., 1976, Molecular Biology of the Gene, W. A. Benjamin, Inc., Menlo Park, California), can be conventionally synthesized by the modified phosphotriester method using fully protected trideoxyribonucleotide building blocks. Such synthetic methods are well known in the art and can be carried out in substantial accordance with the procedure of Itakura et al., 1977, Science 198:1056 and Crea et al., 1978, Proc. Nat. Acad. Sci. USA 75:5765. Those skilled in the art will recognize that other DNA sequences encoding the same amino acids as those encoded by the above illustrative DNA sequence can also be synthesized. These other DNA sequences reflect the degeneracy of the genetic code and thus can be substituted and used for purposes of the present invention.

The aforementioned DNA sequences comprise 1014 bp (m=n=o), 1017 bp (m=o, n=1) or 1020 bp (m=1, n=1) and encode, respectively, the last 338, 339 and 340 amino acids of hygromycin B phosphotransferase. Hereinafter, these DNA sequences are referred to as the "HPT sequences". The amino acids of hygromycin phosphotransferase encoded by the aforementioned sequences, hereinafter referred to as "HPT polypeptides", are also specified above and catalyze the phosphorylation of hygromycin B. Details of this enzymatic reaction and its product are found in Rao et al, 1983, Antimicrob. Ag. Chemother. 2:689. Although hygromycin B in the absence of magnesium ion is lethal to Cephalosporium, the phosphorylated derivative of hygromycin B is not lethal and has neglible effects. Thus, when one of the HPT polypeptide-encoding sequences is expressed in a Cephalosporium, for example, C. acremonium, the cells are rendered resistant to hygromcyin B.

The recombinant DNA cloning vectors used in the present method are characterized, in part, by the presence of a Cephalosporium-functional autonomous replication sequence (ARS). The ARS appears to increase the frequency of genetic transformation of Cephalosporium when present in a vector. This was shown by comparing the transformation frequency obtained with an ARS-containing plasmid, such as, for example, plasmid pIT221, to that obtained with the corresponding desARS-plasmid. Illustrative plasmid pIT221 (See FIG. 1) comprises (in part) (1) an HPT DNA sequence; (2) an E. coli origin of replication, (3) a DNA sequence that codes for a selectable phenotype in E. coli; and (4) a Cephalosporium-functional ARS. Plasmid pIT221 is further characterized by a unique SphI restriction site which occurs outside the above-described sequences and also a ~0.3 kb SmaI fragment that can be deleted or substituted without loss of function. Although the DNA sequence that codes for a selectable phenotype in *E. coli* codes for ampicillin resistance in illustrative plasmid pIT221, other selectable sequences can be substituted. These sequences include, for example, the tetracycline, chloramphenicol, apramycin and like resistance genes available to those skilled in the art.

The Cephalosporium-functional ARS is defined by the ability to impart the capacity for autonomous replication in a lower eukaryote. This is demonstrated by observing automonous replication in a lower eukaryote such as, for example, *Saccharomyces cerevesiae*, of an ARS-containing plasmid derived from a parental plasmid that cannot otherwise replicate in the organism. Although the function of a Cephalosporium ARS may be conveniently assayed in *Saccharomyces cerevisiae*, the preferred lower eukaryote for assay purposes is *C. acremonium*. The preference exists since only a small number of the ARS defined in *S. cerevisiae* can support increased frequency of genetic transformation in *C. acremonium*. In the case of illustrative plasmid pIT221, the function of the Cephalosporium ARS was both assayed in yeast (Skatrud and Queener, 1984, Current Genetics 8:155–163; and Tudzynski and Esser, 1982, Current Genetics 6:153) and was also shown to increase the capacity for transformation of *C. acremonium*. Plasmid pPS5, a pIT221 derivative obtained by removing the ~1.9 kb PstI fragment, lacks the ARS and was only shown capable of transforming Cephalosporium at very low frequencies. Therefore, the ARS component is preferred for purposes of the present invention.

Plasmid pIT221 is further characterized by the presence of a *Saccharomyces cerevisiae* DNA sequence that codes for the transcriptional and translational activating sequence of the phosphoglycerate kinase (PGK) gene. The aforementioned gene, contained in plasmid pIT141, comprises a strong activating sequence that can be conveniently isolated on a MboII fragment. Plasmid pIT141 can be obtained from *E. coli* K12/pIT141, a strain deposited in the permanent culture collection of the Northern Regional Research Laboratories, Peoria, Ill. The strain is available as a stock reservoir and preferred source of the plasmid under the accession number NRRL B-15602. Other *S. cerevisiae* activating sequences can also be used in substitution for the PGK sequence, such as, for example, the transcriptional and translational activating sequences of the yeast heat shock, glycolytic and other metabolic genes. Especially preferred are the YG100 and YG101 genes, the construction of which (incorporated by reference herein), is disclosed in U.S. patent application X-6390A, Ser. No. 640,420, filed Aug. 13, 1984 and Ingolia et al., 1982, Molecular and Cellular Biology 2(11):1388.

Plasmids containing a transcriptional and translational activating sequence have particular utility for constructing transformants that are improved for the production of cephem compounds useful in manufacturing clinically important cephem antibiotics. Even a strong activating sequence from a foreign source will often function poorly, if at all, in Cephalosporium. However, low level expression of a HPT DNA sequence by means of a foreign activating sequence can allow for transient transformation under conditions of hygromycin B selection. When the foreign activating sequence functions poorly, there is strong selective pressure for the insertion of the HPT DNA-containing vector into the Cephalosporium genomic DNA. While not being limited by theory, it is believed that insertion allows for juxtapositioning of a genomic Cephalosporium activating sequence in correct translational reading frame relative to the vector-borne HPT DNA sequence. Transformants bearing such integrated HPT DNA sequences are advantageous because of their great stability with or without selection. By way of example, hygromycin B-resistant transformants produced by genetic transformation of *Cephalosporium acremonium* with pIT221 are sufficiently stable so as to allow propagation even in the absence of hygromycin B. In fact, loss of the new genotype is so rare that over 95% of the cells retain the new genotype after 25 generations under non-selective conditions. Moreover, illustrative *Cephalosporium acremonium*/pIT221 transformant CPC-T1 even retains and expresses the newly acquired gene during the fermentative production of cephem antibiotics.

The efficacy of the present invention can be enhanced by using vectors which further comprise a Cephalosporium ribosomal gene (RG) sequence. The RG DNA sequence can be positioned anywhere in the vector except in regions critical to replication, selection or expression of a product. Because many copies of RG sequences exist in the genome of lower eukaryotes, the RG-containing vector has a high probability of being inserted many times, by homologous recombination, into the Cephalosporium genome. The high probability for multiple insertion of RG sequence-containing vectors, such as, for example, plasmid pPS6, provides a basis for the high frequencies at which these plasmids can transform *C. acremonium*. Plasmid pPS6 is constructed by ligation of a *C. acremonium* RG sequence-containing ~3.7 kb XmaI fragment into XmaI-digested plasmid pIT221. The resultant pPS6 plasmid transforms *C. acremonium* at a higher frequency than that observed with the parental plasmid. In addition, some of the pPS6 transformants exhibit greater tolerance to hygromycin B than do the pIT221 *C. acremonium* transformants. This observation is consistent with the higher number of vector insertions expected with RG-containing vectors. The plasmid pPS6 *C. acremonium* transformants are sufficiently stable for fermentative production of cephem compounds without adding hygromycin B to the fermentation medium.

Skilled artisans will recognize that plasmid pPS6 *Cephalosporium acremonium* transformants are particularly useful when a high gene dosage is needed for prolific expression of foreign DNA. If a lower gene dosage is sufficient or desired for the expression of foreign DNA or if a modest increase in gene dosage is desirable to effect a correspondingly small increase in expression of a *C. acremonium* gene, then plasmid pIT221 is the preferred vector for use. Thus, a variety of useful *C. acremonium* transformants can be constructed using the HPT DNA-containing vectors of the present invention.

Additional vectors wherein the foreign transcriptional and translational activating sequence of plasmid pIT221 is replaced with a *Cephalosporium acremonium* activating sequence are also useful. Such sequences are positioned so as to drive the expression of the HPT DNA sequence. These plasmids have great utility in laboratory manipulations and provide a means for cloning foreign genes, *C. acremonium* genes and *C. acremonium* regulatory DNA sequences. Of particular interest are those DNA sequences which are useful for the fermentative production of cephem compounds serving as intermediates in the manufacture of clinically important cephem antibiotics. Such plasmids have special utility because of the simultaneous presence of the Cephalosporium-functional ARS and the *C. acremonium* transcriptional and translational activating sequence, a combination which allows for transformation without genomic integration.

Transformation by plasmid vectors lacking a Cephalosporium-functional ARS requires integration to maintain the plasmid in a population of dividing Cephalosporium cells. Transformation by plasmid vectors lacking a *C. acremonium* activating sequence also requires integration to allow for proper juxtapositioning of the HPT coding sequence with a genomic activating sequence. In contrast, plasmids comprising a *C. acremonium* activating sequence positioned for expression of the HPT coding sequence are maintained, under selective pressure, as autonomously replicating vectors by virtue of the *C. acremonium*-functional ARS. Selective pressure is applied by exposing the transformants to hygromycin B concentrations at which non-transformed cells will not grow. Expression of the HPT polypeptide is thus independent of genomic integration by virtue of the *C. acremonium* activating sequence on the plasmid. Therefore, such plasmids need only be taken up in a *C. acremonium* cell to produce a successful transformation event. Each event, uptake into the *C. acremonium* cell and integration into the *C. acremonium* genome, occurs at the low frequency of about $10^{-3}$ to $10^{-4}$ or sometimes $10^{-5}$ per cell. Therefore, a transformation that requires both events is quite rare as compared with a transformation requiring only uptake.

Plasmids useful in the present method can be further modified by ligation into a Streptomyces plasmid, such as, for example, plasmid pIJ702 (ATCC 39155). This is done by ligating PstI digests of plasmids pIJ702 and pIT221 to form the illustrative ~13 kb plasmids pETS702 and pPLS221. The latter plasmids are multifunctional and useful as shuttle vectors for transfer of genetic material between *E. coli*, Cephalosporium and many Streptomyces species including related Nocardia, such as, for example, *N. lactamdurans*. Streptomyces and related Nocardia species are transformed in substantial accordance with the teaching of International Publication (of International Patent Application No. PCT/GB79/00095) No. WO79/01169, Example 2. Transformants are conventionally selected for thiostrepton resistance and screened for melanin production according to known methods. Importantly, the *C. acremonium* transformants of the aforementioned shuttle vectors are very stable. Thus, the plasmids are very useful for shuttling key genes from Streptomyces species into *C. acremonium* strains for producing modified penam and cephem compounds normally not found in the fermentation broth of native *C. acremonium* strains.

Skilled artisans will recognize that any Streptomyces cloning vector which comprises a Streptomyces-functional origin of replication and a selectable marker can be substituted for the illustrative plasmid pIJ702 DNA. Many such Streptomyces cloning vectors are known, including, but not limited to, the illustrative vectors in Table I below.

TABLE 1

Streptomyces Plasmids

| Plasmid | Source | Accession Number |
|---|---|---|
| SCP2 | *Streptomyces coelicolor* A3(2) | NRRL* 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| pUC3 | Streptomyces 3022A | NRRL 11441 |
| SLP1 | *Streptomyces lividans* | NCIB** 11417 |
| pNM100 | *Streptomyces virginiae* | NRRL 15156 |
| pEL103 | *Streptomyces granuloruber* A39912.13/pEL103 | NRRL 12549 |

*Agricultural Research Culture Collection (NRRL), 1815 North University Street, Peoria, Illinois 61604, United States of America
**National Collection of Industrial Bacteria (NCIB), Torry Research Station, Post Office Box 31, 135 Abbey Road, Aberdeen AB98DG, Scotland, United Kingdom The method and recombinant DNA shuttle vectors of the present invention are not limited for use in a single species or strain of Cephalosporium, Streptomyces or *E. coli*. To the contrary, the vectors are broadly applicable and can be transformed into host cells of many Cephalosporium, Streptomyces and *E. coli* taxa, particularly the restrictionless strains thereof. Moreover, with respect to Streptomyces and Cephalosporium, many of the strains are economically important and produce compounds such as aminoglycoside, macrolide, β-lactam, polyether, glycopeptide, penam and cepham antibiotics. Streptomyces and related Nocardia are known for their metabolic versatility. Thus, many species of Streptomyces and Nocardia are useful as sources of enzymes which functionalize or modify compounds produced in Cephalosporium.

Restrictionless strains are readily selected and isolated from Streptomyces and related Nocardia taxa by conventional procedures and extensions of principles well known in the art (Lomovskaya et al., 1980, Microbiological Reviews 4:206). Cephalosporium strains are believed to be inherently restrictionless. Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Streptomyces taxa, that produce β-lactam antibiotics and in which the present shuttle vectors are especially useful and can be transformed, include restrictionless cells of, for example: *S. lipmanii* (A16884, MM4550, MM13902), *S. clavuligerus* (cephamycin C, clavulanic acid), *S.* (sometimes classified as *Nocardia lactamdurans* (cephamycins A, B and C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus,* and *S. sioyaensis* (MM 4550 and MM 13902).

Preferred host cells of restrictionless strains of Streptomyces taxa, that produce aminoglycoside antibiotics and in which the present shuttle vectors are especially useful and can be transformed, include restrictionless cells of, for example: *S. kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivo reticuli* var. *cellulophilus* (destomycin A), *S. tenebrarius* (tobramycin, apramycin), *S. lavendulae* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A163136-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of Streptomyces taxa, that produce macrolide antibiotics and in which the present shuttle vectors are especially useful and can be transformed, include restrictionless cells of, for example: *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbo nensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosooreus* (carbomycin), *S. thermotolerans* (carbomycin), and *S. albireticuli* (carbomycin).

Preferred host cells of restrictionless strains of Streptomyces taxa, that produce polyether antibiotics and in which the present shuttle vectors are especially useful and can be transformed, include restrictionless cells of, for example: *S. albus* (A204, A28695A and B, salinomycin), *S. hygroscopicus* (A218, emericid, DE3936), A120A, A28695A and B, etheromycin, dianemycin), *S. griseus* (grisorixin), *S. conglobatus* (ionomycin ), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa, that produce glycopeptide antibiotics and in which the present shuttle vectors are especially useful and can be transformed, include restrictionless cells of, for example: *S. orientalis* and *S. haranomachiensis* (vancomycin); *S. candidus* (A-35512, avoparcin), and *S. eburosporeus* (LL-AM 374).

Preferred host cells of other Streptomyces restrictionless strains, in which the present shuttle vectors are especially useful and can be transformed, include restrictionless cells of, for example: *S. coelicolor, S. granuloruber, S. roseosporus, S. lividans, S. espinosus,* and *S. azureus.*

Preferred host cells of restrictionless strains of Cephalosporium, in which the present vectors are especially useful and can be transformed, include restrictionless cells of, for example, *C. acremonium, C. salmosynnematum* (recently classified as *Emercellopsis salmosynnematum*), *C. chrysogenum* taxa including C-1778, 199, C-0012, C-3259, C-1877, C-0003, C-3479 and ATCC No. 14615, *C. purpurascens, C. acremonium* taxa including C-0007, C-0306, C-4653, C-4473, C-5454, and especially CMI 49137 (ATCC 11550) and its derivatives, particularly strains M8650 (ATCC 14553) and its derivatives, and *C. curtipis* (C. sp. S-0161). In addition, other species of *Cephalosporium* such as, for example, *C. chrysogenes* and *C. polyaleusans* can also be used. These taxa produce enzymes known to deaminate and decarboxylate cephalosporin C. The enzymes allow for the production of cephalosporins that can be extracted into organic solvent at low pH and used as substrates for amidases that hydrolyze the side chain of cephalosporin at the 7-amino position to produce 7-ACA and glutarate. The convenience and efficiency of both extraction into organic solvent and enzymatic side chain-cleavage are economically important factors. The ease of processing penicillin V (and G) in the manufacture of oral cephalosporins stems in part from their extractibility to organic solvent and their ability to serve as substrate for amidases that hydrolyze to 6-APA and phenoxyacetate (or phenylacetate).

In addition to the representative Streptomyces, Nocardia and Cephalosporium host cells described above, the present vectors are useful and can transform various strains of fungi and also *E. coli* such as, for example, *E. coli* K12 RR1, *E. coli* K12 JA221, *E. coli* K12 C600, *E. coli* K12 C600R$_k$-M$_k$-, *E. coli* K12 HB101, *E. coli* K12 RV308 and like strains. Preferred host cells of penicillin-producing fungi, in which the present vectors are useful and can be transformed, include *Aspergillus* such as *A. nidulans*, *Penicillium* taxa especially *P. chrysogenum* and *P. notatum*, *Trichophyton*, *Epidermophyton*, *Malbrachea*, *Emercicella*, *Eupenicillia*, *Talomyces*, *Polypaecilum*, *Thermoascus* and *Gymnoascus*. Preferred host cells of cephalosporin-producing fungi, in which the present vectors are useful and can be transformed, include, in addition to the aforementioned *Cephalosporium* taxa, *Paecilomyces* such as *P. persicinus*, *Arachnomyces*, *Anixiopsis*, and *Spiroidium*. Thus, the method and vectors of the present invention have wide application with respect to host cells of a variety of organisms.

The very broad antibiotic spectrum of hygromycin B, the common existence of a PGK gene in most fungi, and the basal level of expression of HPT coding sequences allowed by even minor conservation in the transcriptional and translational activating sequences of phosphoglycerate kinase genes of lower eukaryotes, makes the present invention broadly applicable to a wide variety of fungi. In particular, the present invention can be applied (1) to the improvement of fermentations of *Saccharomyces uvarum* and related yeasts used for the production of alcoholic beverages and alcoholic fuels; (2) to the improvement of Aspergillus fermentations used for the production of citric acid; (3) to the improvement of *Penicillium stoloniferum* fermentations used for the production of mycophenolic acid; and (4) to the improvement of fermentations of a variety of fungi employed to produce commercial enzymes.

The present invention is especially useful for organisms that are not well characterized genetically and biochemically because prior isolation of auxotrophic mutants and genes to complement auxotrophic deficiencies is not required. Furthermore, lower eukaryotes are killed very effectively by hygromycin B and most, particularly fungi, do not exhibit a significant capacity to acquire a natural resistance to hygromycin B by forward mutation. *Cephalosporium acremonium* is killed, in the absence of magnesium and other ions that antagonize the toxic effects, by about 8 μg/ml to about 5 mg/ml of hygromycin B. No forward mutations to hygromycin B resistance have been observed within this range or at the preferred concentration of 100 μg/ml. This absence of forward mutation to resistance is a very important parameter in the application of the present transformation system to commercially important lower eukaryotes. Rare transformants in a high "background" of resistant mutants arising by forward mutations would make the transformants very difficult to detect, isolate, analyze, and manipulate. Since the time and expense required to develop a transformation system for each lower eukaryote with poorly defined genetics and biochemistry can be significant, the present invention has great utility because of its general applicability to a wide variety of such eukaryotic organisms.

The hygromycin phosphotransferase gene product expressed by plasmids pIT221, pPS5, pPS6, pETS702 and pLS221 not only is useful for purposes of selection but also as a molecular weight marker. The entire amino acid sequence of the hygromycin gene product is known and the molecular weight of the protein is ~37,972 daltons. The hygromycin phosphotransferase enzyme may be conventionally purified in substantial accordance with the teachings of Haas and Downing, 1978, Methods in Enzymology, 48:611. The molecular weight of the hygromycin phosphotransferase protein is conveniently between the highest molecular weight of Bio-Rad's (32nd and Griffin Ave., Richmond, CA 94804-9989) Low Molecular Weight Protein Standards and the lowest molecular weight of Bio-Rad's High Molecular Weight Protein Standards. Bio-Rad's protein standards are quite well known in the art and the hygromycin resistance gene product of the aforementioned plasmids conveniently expands the size range of either the Low or High Molecular Weight Protein Standards.

The following examples and construction flow sheets further illustrate and detail the invention discribed herein. Both an explanation of and the actual procedures for constructing the invention are described where appropriate.

Construction Flow Sheet I

Method for constructing plasmid pKC222—an intermediate used in the cosntruction of plasmid pIT221—from plasmid pKC7 (ATCC 37084) and plasmid pKC203-containing *E. Coli* JR225 (ATCC 31912)

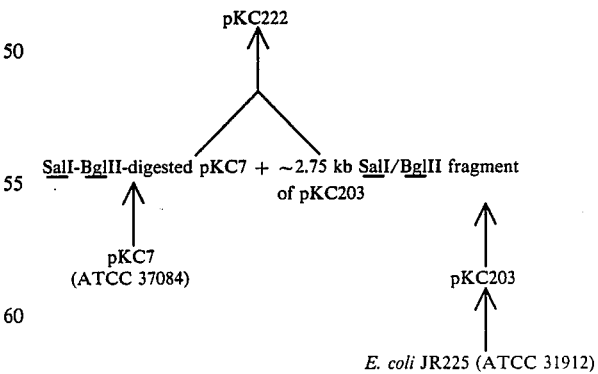

Construction Flow Sheet II

Method for constructing plasmid pIT123—an intermediate used in the constuction of plasmid pIT221—from plasmids pBR322 and pKC222

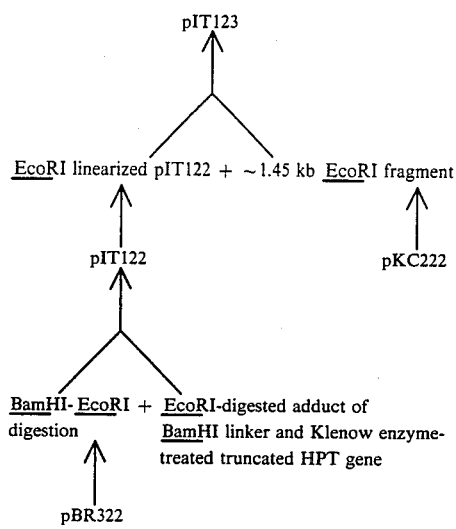

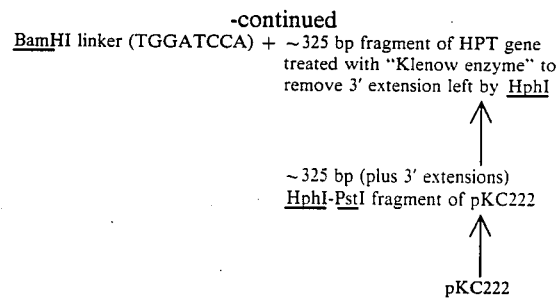

-continued

BamHI linker (TGGATCCA) + ~325 bp fragment of HPT gene treated with "Klenow enzyme" to remove 3' extension left by HphI
↑
~325 bp (plus 3' extensions) HphI-PstI fragment of pKC222
↑
pKC222

Construction Flow Sheet III

Method for constructing plasmid pIT143—an intermediate used to construct plasmid pIT221—from plasmids pUC8 and pIT141 (NRRL-B-I5602)

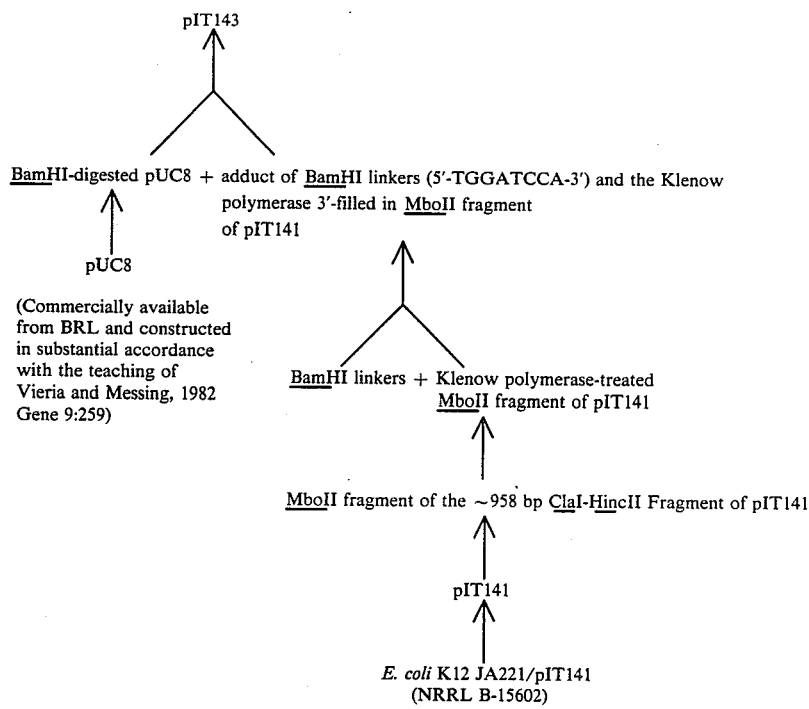

CONSTRUCTION Flow Sheet IV

Method for constructing plasmid pIT213—an intermediate used to construct plasmid PIT221—from plasmids YEp24 (pRB5, ATCC 37051) and pIT123

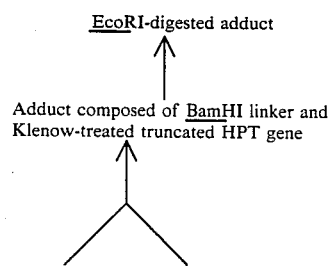

-continued

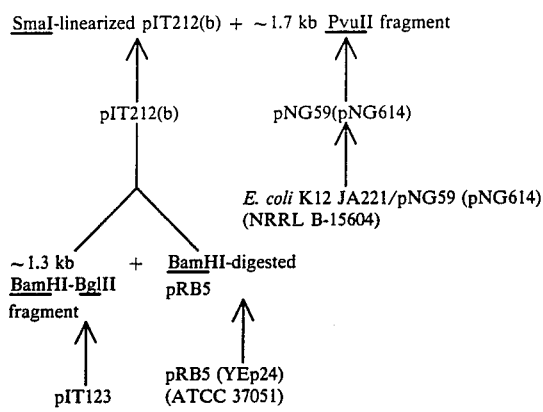

Construction Flow Sheet V

Method for construction pPS1—an intermediate used to construct plasmid pIT221—from plasmid YIp5 (pRB12, ATCC 37061) and *Cephalosporium acremonoum* (ATCC 11550)

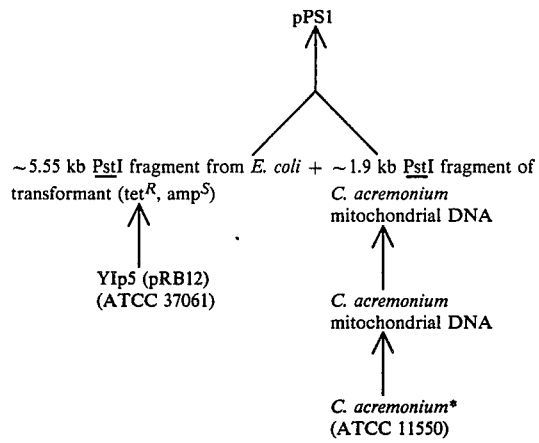

Note:

*Although strains of *C. acremonium* highly developed for production of cephalosporin C can also be used as a source of the *C. acremonium* ARS (Skatrud and Queener, 1984), ATCC 11550 is preferred because of its fast growth and ease of propagation.

Construction Flow Sheet VI

Method for constructing plasmid pIT221 from plasmids pUC8, pPS1, pIT213 and pIT143

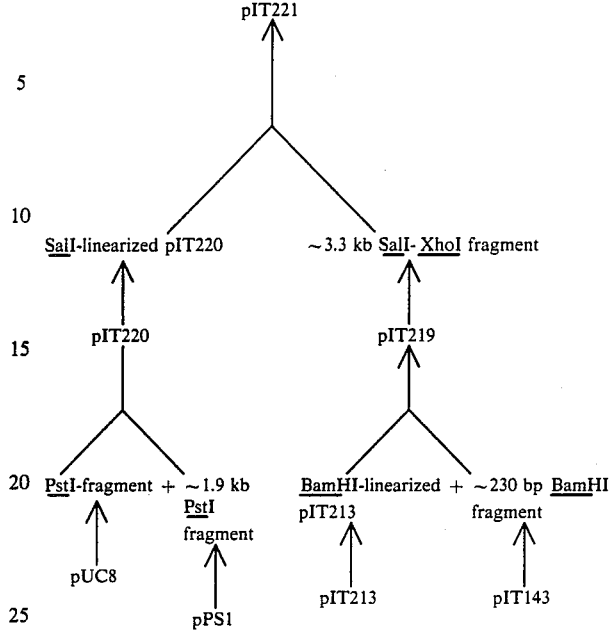

EXAMPLE 1

Construction of Plasmid pKC222

A. Isolation of Plasmid pKC203 and Construction of *E. coli* K12 BE827/pKC203

The bacterium *E. coli* JR225 (ATCC No. 31912) was cultured in TY broth (1% tryptone, 0.5% yeast extract, 0.5 ml sodium chloride, pH 7.4) with 100 μg/ml of antibiotic hygromycin B according to conventional microbiological procedures. After 18 hours incubation, about 0.5 ml of the culture was transferred to a 1.5 ml Eppendorf tube and centrifuged for about 15 seconds. Unless otherwise indicated, all the manipulations were done at ambient temperature. The resultant supernatant was carefully removed with a fine-tip aspirator and the cell pellet was suspended in about 100 μl of freshly prepared lysozyme solution which contained 2 mg/ml lysozyme, 50 mM glucose, 10 mM CDTA (cyclohexane diaminetetracetate) and 25 mM Tris-HCl (pH 8.0). After incubation at 0° C. for 30 minutes, about 200 μl of alkaline SDS (sodium dodecyl sulfate) solution (0.2N NaOH, 1% SDS) were added. The tube was gently vortexed, maintained at 0° C. for 15 minutes and then about 150 μl of 3M sodium acetate solution (prepared by dissolving 3 moles of sodium acetate in a minimum of water and adjusting the pH to 4.8 with glacial acetic acid and then the volume to 1 L) were added. The contents of the tube were mixed gently by inversion for a few seconds during which time a DNA clot formed.

The tube was maintained at 0° C. for 60 minutes and then centrifuged for 5 minutes to yield an almost clear supernatant. About 0.4 ml of the supernatant was transferred to a second centrifuge tube to which 1 ml of cold ethanol was added. After the tube was held at −20° C. for 30 minutes, the resultant precipitate was collected by centrifugation (2 minutes) and the supernatant was removed by aspiration. The collected pellet was dissolved in 100 μl of 0.1M sodium acetate/0.05M Tris-HCl (pH 8) and was reprecipitated by the addition of 2 volumes of cold ethanol. After 10 minutes at 20° C., the desired *E. coli* JR225 plasmid DNA precipitate was collected by centrifugation as described above.

The *E. coli* JR225 plasmid DNA pellet was dissolved in about 40 μl of water or dilute buffer and then used to transform *E. coli* K12 BE827 in substantial accordance with the transformation method of Wensink, 1974, Cell 3:315. The strain *E. coli* K12 BE827 has been deposited and made part of the permanent stock culture collection of the American Type Culture Collection, Rockville, Maryland and is available to the public under the number ATCC 31911. The resultant transformants were selected on TY agar (1% tryptone, 0.5% yeast extract, 0.5% sodium chloride, 1.5% agar, pH 7.4) containing 200 μg/ml of antibiotic hygromycin B. Some of the transformants, as shown by gel electrophoresis (Rao and Rogers, 1978, Gene 3:247) and other tests, contained both large and small (~15 kb) plasmids and were resistant to both antibiotics ampicillin and hygromycin B. Other transformants contained only the smaller ~15 kb plasmid and were resistant to antibiotics hygromycin B and G418 but were sensitive to ampicillin.

Transformants of the latter type were plated on TY agar containing 100 μg/ml of antibiotic hygromycin B and were cultured using standard microbiological techniques. The resultant cells were used to isolate the above described ~15 kb hygromycin B and G418 resistance-conferring plasmid, hereinafter designated as plasmid pKC203. The presence of the antibiotic hygromycin B and G418 resistance genes on plasmid pKC203 was confirmed by subsequent transformation and selection analysis.

B. Construction of Plasmid pKC222 and Transformant *E. coli* K12 JA221/pKC222

1. Isolation of the ~2.75 kb SalI/BglII Fragment of Plasmid pKC203

About 5 μg of plasmid pKC203 DNA were digested in a total reaction volume of 100 μl with BglII restriction enzyme in IX BglII buffer* at 37° C. for about 2 hours. Completion of digestion was ascertained by agarose gel electrophoresis. After complete digestion, the NaCl concentration was increased to 0.15M by addition of 2 μl of 5M NaCl. About 10 units of SalI restriction enzyme were then added followed by a second digestion at 37° C. for 2 hours. An ~2.75 kb fragment contains the genes and control elements for resistance to antibiotics hygromycin B and G418 and can be recovered by agarose gel electrophoresis and other conventional procedures (Maniatis et al., 1982, Molecular Cloning, Cold Spring Harbor Laboratory, Cold Spring Harbor, New York).

---

*10X BglII reaction buffer was prepared with the following composition and was diluted to the desired 1X concentration
  .5M NaCl
  .5 M Tris-HCl, pH 7.4
  .1 M MgCl₂
  .01 M Dithiothreitol

---

2. Ligation and Final Construction

About 5 μg of plasmid pKC7 (ATCC 37084), which can be constructed in accordance with the teaching of Rao and Rogers, 1979, Gene 7:79, were treated with SalI and BglII restriction enzymes in substantial accordance with the teaching of Example 1B(1). After the enzymes were inactivated by heating at 70° C. for 5 minutes, about 1 μg of the DNA was mixed in a 1:1 ratio with the ~2.75 kb SalI/BglII fragment of pKC203. The fragments were joined in a total reaction volume of 25 μl in IX ligation buffer* with 1 Weiss unit of T DNA ligase at 4° C. for about 16 hours. The resulting plasmid pKC222 was transformed into *E. coli* K12 JA221 (NRRL B-15211) in substantial accordance with the teaching of Example 1A. The resultant transformants were selected on TY agar (1% typtone 0.5% yeast extract, 0.5% NaCl, 1.5% agar) containing 50 μg/ml of antibiotic ampicillin. Transformants were then screened for then desired plasmid.

---

*10X Ligation buffer was prepared with the following composition and was diluted to the desired 1X concentration.
  .3 M Tris-HCl, pH 8
  .07 M MgCl₂
  .012 M EDTA
  .005 M ATP
  .01 M Dithiothreitol

---

3. Isolation of Plasmid pKC222

Purified transformants were cultured in TY broth (1% tryptone, 0.5% yeast extract, 0.5% sodium chloride, pH 7.4%) with 50 μg/ml of antibiotic ampicillin according to conventional microbiological procedures. After 18 hours incubation, the desired plasmid was isolated in substantial accordance with the teaching of Example 1A.

EXAMPLE 2

Construction of Plasmid pIT123 and *E. coli* K12 JA221/pIT123

A. Isolation of the HhI-PstI Fragment of Plasmid pKC222

About 50 μg of plasmid pKC222 DNA were digested in IX HphI salts (6 mM KCl, 10 mM Tris-HCl, pH 7.4, 10 mM MgCl₂, 1 mM Dithiothreitol) in a total volume of 100 μl with 20 New England Biolab Units of HhI restriction endonuclease. Completion of digestion was checked by electrophoresing 2% of the reaction mixture on agarose. After the NaCl concentration was adjusted to 60 mM by addition of an appropriate volume of 5M NaCl, about 20 units of PstI restriction endonuclease were added. Completion of digestion was again monitored by agarose gel electrophoresis. The desired ~325 bp (plus single stranded extensions) HphI-PstI fragment was purified from acrylamide using standard techniques (Schlief and Wensink, 1981, Practical Methods in Molecular Biology. Springer-Verlag, NY).

The purified ~325 bp fragment was treated with the large fragment of DNA Polymerase I (New England Biolabs). Thus, about 1.5 μl (1 μg) of fragment, 0.5 μl of 10× buffer (0.5M Tris, pH 7.5, 0.1M MgCl₂), 0.5 μl of each of (200 mM) dCTP, dATP, TTP and dGTP and 1 μl (containing 1 unit) of DNA polymerase I large (Klenow) fragment were incubated at 37° C. for 15 minutes. After heat inactivation of the polymerase, BamHI linkers were added in substantial accordance with the procedure of Roberts and Lauer, 1979, Methods in Enzymology 68:473. The resultant BamHI linker-containing DNA was conventionally digested with BamHI restriction enzyme in 1× BamHI salts (150 mM NaCl, 6 mM Tris-HCl, pH 7.9, 6 mM MgCl₂). Next, the Tris-HCl concentration was increased to 100 mM with an appropriate volume of 2M Tris-HCl, pH 7.4 and then the DNA was further digested with EcoRI restriction enzyme. The resultant digested DNA was again electrophoresed on a 7% acrylamide gel and the desired ~250 bp fragment was purified as before.

Construction of Plasmid pIT122 and E. coli K12 JA221/pIT122

About 2 μg of pBR322 DNA were sequentially digested with BamHI and EcoRI restriction enzymes in substantial accordance with the teaching of Example 2A. After the enzymes were inactivated by heating at 70° C. for 5 minutes, about 1 μl (1 μg) of the pBR322 DNA was mixed with about 1 μl (1 μg) of the purified ~250 bp fragment, 37 μl water, 5 μl (10 mM) ATP, 5 μl ligation mix (0.5 Tris-HCl, pH 7.8, 0.2M dithiothreitol, 0.1M MgCl₂), and 1 μl T4 DNA ligase (approximately 1,000 New England Biolabs Units). The mixture was incubated at 15° C. for about 2 hours and then the reaction was terminated by incubation at 70° C. for 5 minutes. After cooling on ice, the resultant ligated mixture was used to transform E. coli K12 JA221 (NRRL B-15211) in substantial accordance with the transformation procedure of Wensink, 1974, on TY plates containing ampicillin at 50 μg/ml. The identity of the desired transformants was conventionally confirmed by testing for the expected phenotype (Amp$^R$, Tet$^S$) and also for the appropriate EcoRI-BamHI insert. The resultant E. coli K12 JA221/pIT122 transformants were conventionally cultured for subsequent production and isolation of plasmid pIT122.

C. Ligation of 1.5 kb EcoRI Fragment of Plasmid pKC222 into EcoRI-Digested Plasmid pIT122

Figure 2:
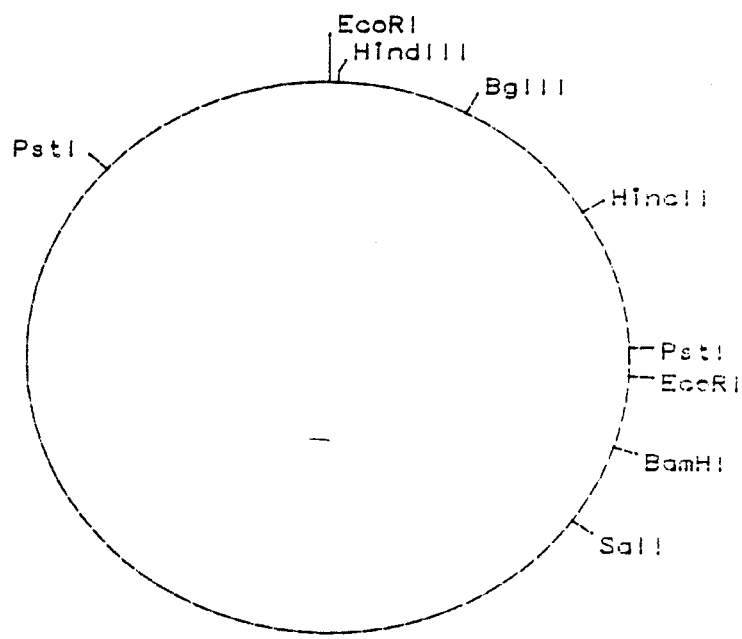
FIG. 2—Restriction Site Map of Plasmid pIT123.

About 20 μg of plasmids pKC222 and pIT122 were independently cleaved in separate reaction volumes of 200 μl each with 40 units EcoRI restriction enzyme in 1× EcoRI reaction mix (0.1M Tris-HCl, pH 7.5, 0.05M NaCl, 0.005M MgCl₂). The desired ~1.45 kb EcoRI fragment was conventionally purified from a 7% acrylamide gel and ligated into the EcoRI-digested pIT122. The resultant ligated DNA was designated as plasmid pIT123 and was then used to transform E. coli K12 JA221 (NRRL B-15211). Both the ligation and transformation procedures were carried out in substantial accordance with the teaching of Example 2B. The ampicillin resistant transformants were conventionally screened for the presence and correct orientation of the ~1.45 kb EcoRI fragment by restriction enzyme and agarose gel electrophoretic analysis of the constitutive plasmids. Plasmids containing the entire hygromycin B resistance gene, except for the first 9 base pairs, constituted the desired plasmid pIT12.3. The thus identified E. coli K12 JA221/pIT123 transformants were then cultured for subsequent production and isolation of plasmid pIT1123. A restriction site map of plasmid pIT123 is presented in FIG. 2 of the accompanying drawings.

EXAMPLE 3

Construction of Plasmid pIT143

A. Isolation of Plasmid pIT141

Plasmid pIT141 contains the entire Saccharomyces cerevisiae phosphoglycerate kinase (PGK) gene and is used to construct-plasmid pIT143. The plasmid can be conventionally isolated from E. coli K12 JA221/pIT141, a strain deposited and made part of the permanent stock culture collection of the Northern Regional Research Laboratory, Peoria, Illinois. The strain is available to the public as a preferred source and stock reservoir of plasmid pIT141 under the accession number NRRL B-15602. Plasmid pIT141 confers ampicillin resistance and is isolated in substantial accordance with the teaching of Example 1.

B. Construction of Plasmid pIT143

Plasmid pIT143, from which the Saccharomyces cerevisiae PGK transcriptional and translational activator sequence is obtained, is constructed by digesting (in a total reaction volume of 200 μl) about 50 μg of plasmid pIT141 DNA in 1× BglII buffer with 100 units of HincII restriction enzyme at 37° C. for about 2 hours. Completion of digestion was monitored by agarose gel electrophoresis. After complete digestion, the NaCl concentration was increased to 0.15M by the addition of 4 μl of 5M NaCl solution. About 100 units of ClaI restriction enzyme was then added and digestion was continued at 37° C. for an additional 2 hours. When digestion was complete, the resultant ~958 bp ClaI-HincII fragment was conventionally isolated from an acrylamide gel and purified in accordance with known methods (Maniatis et al., 1982).

About 5 μg of the purified ~958 bp ClaI-HincII fragment was then digested with 20 units of MboII restriction enzyme in 1× MboII reaction buffer* in a total volume of 50 μl at 37° C. for about 2 hours. The resultant MboII-cleaved DNA was then conventionally purified by a phenol extraction, 2 chloroform extractions and 2 ethanol precipitations. The purified DNA was then suspended in 20 μl of 1× Klenow buffer and treated with 0.5 units of E. coli DNA polymerase I large fragment (Klenow) for 30 minutes at 37° C. The DNA was precipitated once with ethanol and then suspended in 25 μl of 1× ligation buffer with about 30 pmoles of phosphorylated BamHI linker, (sequence TGGATCCA, single strand shown for convenience), synthesized in substantial accordance with the teaching of Itakura et al., 1977 and Crea et al., 1978. Ligation was carried out in substantial accordance with the teaching of Example 1B(2). The ligated DNA was then cleaved by diluting the ligation mix to 100 μl with 1× BamHI buffer* and adding 100 units of BamHI restriction enzyme. After digestion at 37° C. for about 3 hours, the mixture was electrophoresed on a 7% acrylamide gel and the ~230 bp fragment containing the PGK gene promoter was conventionally isolated and purified (Maniatis, 1982).

Figure 3:
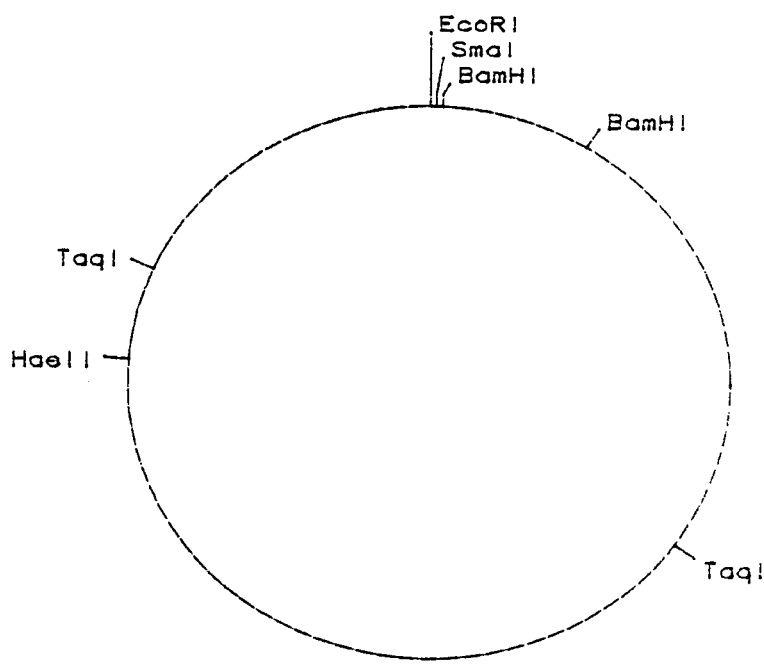
FIG. 3—Restriction Site Map of Plasmid pIT143.

In a separate tube, about 1 μg of plasmid pUC8 (commercially available from BRL) was digested with 5 units of BamHI restriction enzyme in BamHI reaction buffer at 37° C. for about 1 hour. The BamHI-cleaved pUC8 was then ligated with the ~230 bp BamHI fragment in substantial accordance with the teaching of Example 1B(2). The resulting plasmid, designated as plasmid pIT143, was conventionally isolated and purified for further use. The relevant DNA sequence of pIT143, beginning with the translation initiation site, was found to be 5'-ATG GAT CC-3'. The BamHI site of pIT143 is in phase with the BamHI site of the truncated hygromycin resistance-conferring gene on pIT143 is presented in FIG. 3 of the accompanying drawings.

---

*10X MboII reaction buffer was prepared with the following composition and was diluted to the desired 1X concentration.
   .06 M KCl
   .1 M Tris-HCl, pH 7.9
   .1 M MgCl$_2$
   .01 M Dithiothreitol
**10X Klenow buffer was prepared with the following composition and was diluted to the desired 1X concentration.
   .4 M KPO$_4$, pH 7.5
   .03 M MgCl$_2$
   .01 M 2-mercaptoethanol
   .31 mM of each of dCTP, dATP, dTTP and dGTP
***10X BamHI reaction buffer was prepared with the following composition and was diluted to the desired 1X concentration.
   1.5 M NaCl
   .5 M Tris-HCl, pH 7.4
   .1 M MgCl$_2$
   .01 M Dithiothreitol

---

EXAMPLE 4

Construction of Plasmid pIT213

The kanamycin resistance gene from Tnl(903) was incorporated into plasmid YEp24 (RB5, ATCC 37051) by purifying an ~1.7 kb PvuII fragment from plasmid pNG614 (NRRL B-15604) and ligating it into the unique SmaI site of plasmid YEp24. The truncated hygromycin gene was also added by ligating an ~1.3 kb BamHI-BglII fragment from plasmid pIT123 into the unique BamHI site.

Figure 4:
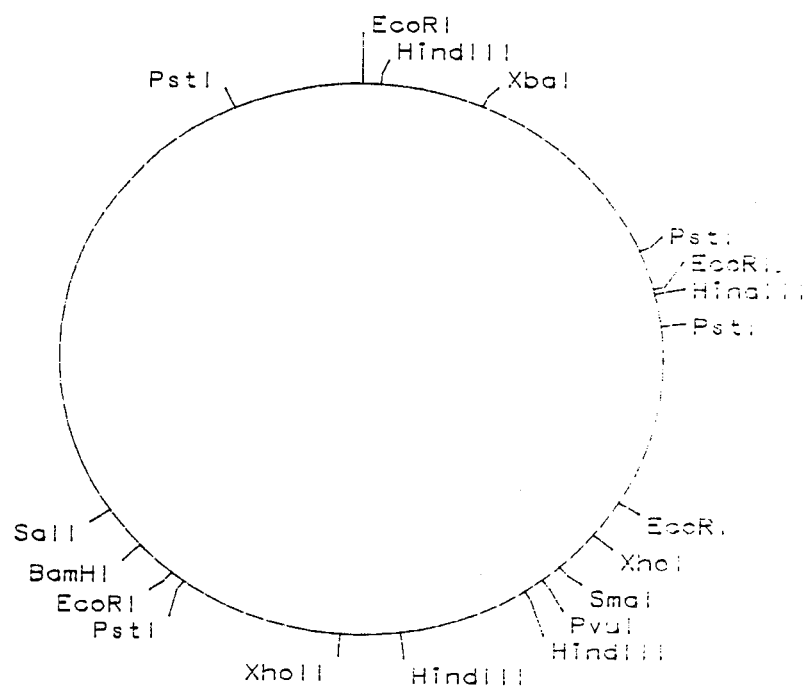
FIG. 4—Restriction Site Map of Plasmid pIT213.

The PvuII, BamH, BglII and SmaI digestions and the required fragment isolations were carried out in substantial accordance with the teaching of Example 1B(1) except that PvuII* and SmaI** reactions buffers (Maniatis, et al., 1982) were substituted for the BglII reaction buffer where appropriate. The ligation procedures were carried out in substantial accordance with the teaching of Example 1B(2). A restriction site map of plasmid pIT213 is presented in FIG. 4 of the accompanying drawings.

EXAMPLE 5

Construction of Plasmid pPS1

A. Isolation of Plasmid pRBb 1 (YIp5) ATCC No. 37061

The bacterium *E. coli* K12 RR1 (NRRL B-15210) was cultured in L broth (Bacto tryptone 1%, Bacto Yeast Extract 0.5%, sodium chloride 1%) according to conventional microbiological procedures. After 16 hours incubation, the cells were harvested by centrifugation and transformed with plasmid pRB12 (YIp5) DNA (obtained from ATCC) in substantial accordance with the method of Mandel and Higa, 1979, J. Mol. Biol. 53:154%. Transformants were selected on minimal medium supplemented with 50 μg/ml of the antibiotic ampicillin.

A transformant was isolated and cultured in the presence of ampicillin according to conventional microbiological procedures. The plasmid pRB12 (YIp5) DNA was isolated from this culture in substantial accordance with the method of Clewell, 1972, Journal of Bacteriology 110:667. Transformation and restriction analysis confirmed the identity of the DNA as plasmid pRB12 (YIp5).

B. Isolation of Cehalosporium acremonium Mitochondrial DNA

The antibiotic-producing filamentous fungus *Cephalosorium acremonium* (any *C. acremonium* strain, particularly ATCC 11550 and ATCC 14553 is acceptable) was cultured in TS broth (BRL trypticase soy broth 3%, potassium phosphate 0.035%, pH 6.7) according to standard microbiological procedures. After 48 hours growth, the mycelia were harvested by suction filtration through a Whatman No. 1 filter supported in a Buchner funnel. The mycelial mat was washed two times with an equal volume of TE buffer (10 mM Tris pH 7.9, 10 mM Na$_2$EDTA). Total DNA was isolated from 80 grams of mycelia in substantial accordance with the method of Minuth et al., 1982, Current Genetics 5:227. Mitochondrial DNA was separated from chromosomal by cesium chloride equilibrium centrifugation (45,000 rpm, 65 hr) in the presence of 0.33 mg propidium iodide/ml. This procedure produced a large chromosomal band and a smaller denser band which contained predominantly mitochondrial DNA. The mitochondrial DNA band was removed by side puncture, extracted six times with an equal volume of isopropanol saturated with cesium chloride to remove the propidium iodide, dialyzed about 16 hours against TE buffer to remove the cesium chloride and then ethanol precipitated. The presence of mitochondrial DNA was conventionally demonstrated by restriction analysis (Skatrud and queener, 1984, Current , Genetics 8:155).

C. Construction of Plasmid pPS1 and Transformant *E. coli* K12 HB101/pPS1

1. Isolation of the ~1.9 kb PstI fragment from Cephalosporium acremonium mitochondrial DNA Approximately 35 μg of *Cephalosporium acremonium* mitochondrial DNA were treated with the restriction enzyme PstI in substantial accordance with the teaching of Example 2A except that only PstI, rather than PstI and HphI, was used in the digestion. The ~1.9 kb PstI fragment was isolated from an agarose gel by electroelution onto DEAE cellulose paper (Whatman). The DEAE paper strip with the bound DNA was washed twice with 100 mM KCl, 0.1 mM EDTA, 10 mM TRIS, pH 7.9. DNA was eluted from the DEAE paper with 4 ml of 1.0M NaCl, 0.1 M EDTA, 10 mM TRIS, pH 7.9 and ethanol precipipated by the addition of a tenth volume 3M sodium acetate, pH 8.0 and two volumes ice cold ethanol. This mixture was incubated at −70° C. for 30 minutes. The DNA was harvested by centrifugation (16,000× g, 25 min.) and resuspended in TE buffer.

2. Isolation of PstI linearized pRB12

The plasmid pRB12 (YIp5, ATCC No. 37061) contains two sites for the restriction enzyme PstI, one in the ampicillin resistance gene and the other in the yeast URA3 gene. To ligate the ~1.9 kb Pst1 fragment from *Cephalosporium acremonium* mitochondrial DNA into the PstI site of the ampicillin resistance gene, a partial PstI digest of 30 μg of pRB12 (YIp5) was performed in a buffer solution containing 20 mM Tris-HCl, p 7.5, 10 mM MgCl$_2$, 50 mM (NH)$_2$SO$_4$, 100 μg BSA and 750 units of PstI restriction enzyme. After digestion at 37° C. for 3 minutes, the reaction was terminated by heating at 65° C. for 10 minutes. The mixture of full length linear fragments was gel isolated as described above.

3. Ligation and Final Concentration

Approximately 1 μg of the ~1.9 kb PstI fragment of *Cephalosporium acremonium* DNA was mixed with an equal amount of of PstI linearized pRB12 (YIp5) DNA. These DNA fragments were joined using T4 DNA ligase in substantial accordance with the teaching of Example 2A. The resulting plasmids, a mixture of recircularized parental plasmid and plasmid pRB12 (YIp5) with the ~1.9 kb PstI mitochondrial fragment inserted at either the PstI site in the ampicillin gene or the yeast URA3 gene, is used to transform *E. coli* K12 RR1 (NRRL B-15210) to tetracycline resistance in substantial accordance with the method of Mandel and Higa, 1979, J. Mol. Biol. 53:154. Tetracycline resistant transformants are screened for insertional inactivation of ampicillin resistance according to the method of Boyko and Ganschow, 1982, Analytical Biochemistry 122:85-88.

Figure 5:
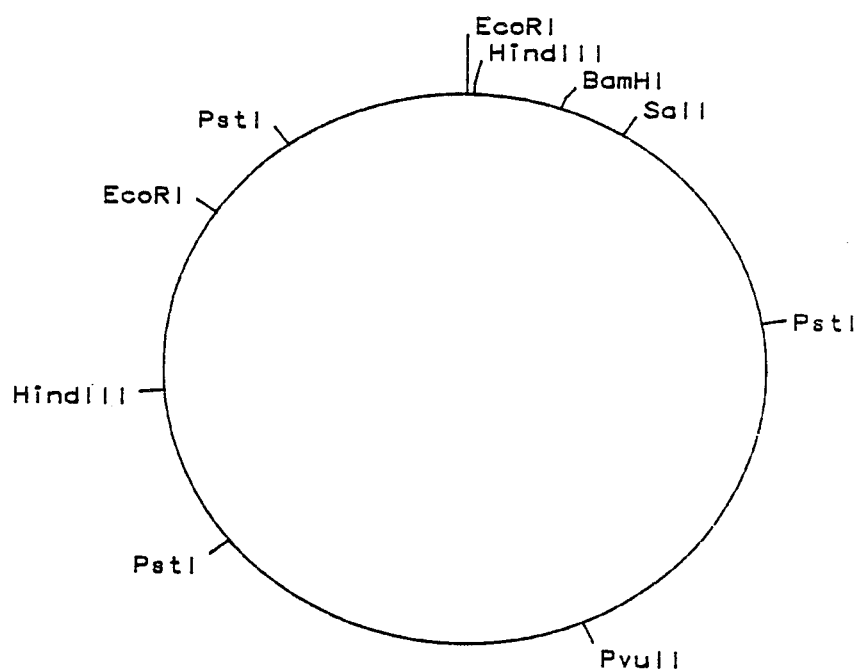
FIG. 5—Restriction Site Map of Plasmid pPS1.

A purified tetracycline resistant, ampicillin sensitive transformant is cultured under selective conditions (i.e., with tetracycline at 12.5 μg/ml). Small scale plasmid preparations are made in substantial accordance with the method of Klein et al., 1980, Plasmid 3:88 and screened by restriction analysis to determine which plasmid preparations contained the ~1.9 kb Pst1 fragment at the correct position of insertion. After identification of an isolate carrying the desired plasmid, a large scale plasmid DNA isolation is performed in substantial accordance with the method of Clewell, 1972, Journal of Bacteriology 110:667 to produce plasmid pPS1. The structure of plasmid pPS1 was verified by restriction analysis and hybridization analysis as detailed in Skatrud and Queener, 1984. The plasmid was used to transform the yeast strain DBY-746 (ATCC 44773) to uracil independence in substantial accordance with the method of Beggs, 1978, Nature 275:104. The frequency of transformation along with hybridization analysis demonstrates that plasmid pPS1 is capable of autonomous replication in yeast. A restriction site map of plasmid pPS1 is presented in FIG. 5 of the accompanying drawings.

EXAMPLE 6

Construction of Plasmid pIT221

A. Construction of Plasmid pIT220

1. Purification of the ~1.93 kb PstI Fragment of Plasmid pPS1

About 20 μg of pPS1 were digested in PstI digestion buffer (0.1M NaCl, 0.5M Tris-HCl pH 8, 0.01M MgCl$_2$) with 50 units of PstI restriction endonuclease at 37° C. until digestion was complete. The ~1.93 kb PstI fragment was isolated and purified from polyacrylamide using standard procedures (Maniatis et al., 1982).

2. Digestion of Plasmid pUC8 with PstI

About 5 μg of pUC8 (commercially available from Bethesda Research Laboratories, Bethesda, Maryland and prepared by the same method as described for the isolation of the plasmid pKC203 in Example 1) was digested in substantial accordance with the above teaching of Example 6A.

3. Ligation of the ~1.93 kb Pst1 Fragment from Plasmids pPS1 into pUC8

Figure 6:
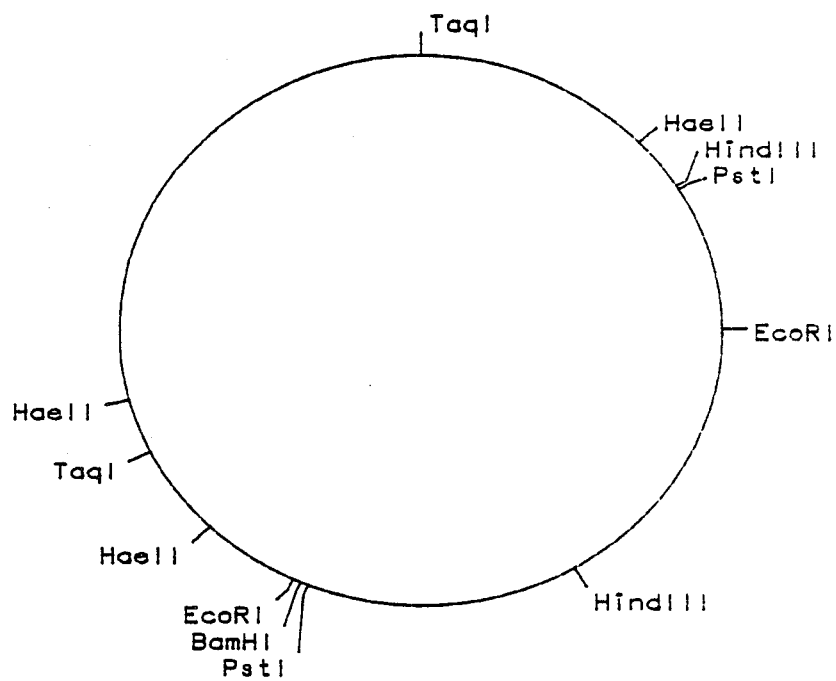
FIG. 6—Restriction Site Map of Plasmid pIT220.

About 1 μg of PstI-cleaved pUCS and 0.1 μg of the ~1.93 kb Pst1 fragment from pPS1 were incubated with 1000 (New England Biolabs) units of T4 DNA ligase in buffer (20 mM Tris-HCl, pH 7.6, 10 mM MgCl$_2$, 0.5 mM ATP, 10 mM dithiothreitol) in 30 μl total volume at 15° C. for 2 hours. The DNA was then used to transform *E. coli* K12 RRI (NRRL B-15210) and the desired plasmid pIT220 was isolated and prepared from the resulting ampicillin resistant *E. coli* transformants using the procedure of Example 1A. A restriction site map of plasmid pIT220 is presented in FIG. 6 of the accompanying drawings.

B. Construction of Plasmid pIT221

1. Isolation of BamHI-linearized plasmid pIT213

About 5 μg of pIT213 were digested in BamHI digestion buffer (150 mM NaCl, 6 mM Tris-HCl pH 7.9, 6 mM MgCl$_2$ and 150 μg/ml bovine serum albumin) with 25 units of BamHI restriction endonuclease in 50 μl volume at 37° C. until digestion was complete. The linearized plasmid pIT213 was conventionally isolated and purified by agarose gel electrophoresis.

2. Isolation of the ~230 bp BamHI fragment of plasmid pIT143

Approximately 5 μg of pIT143 were digested with BamHI restriction endonuclease in substantial accordance with the teaching of Example 5B(1). The fragment was conventionally isolated by polyacrylamide gel electrophoresis.

3. Ligation of BamHI-linearized plasmid pIT213 to the ~230 bp BamHI fragment of plasmid pIT143

Figure 7:
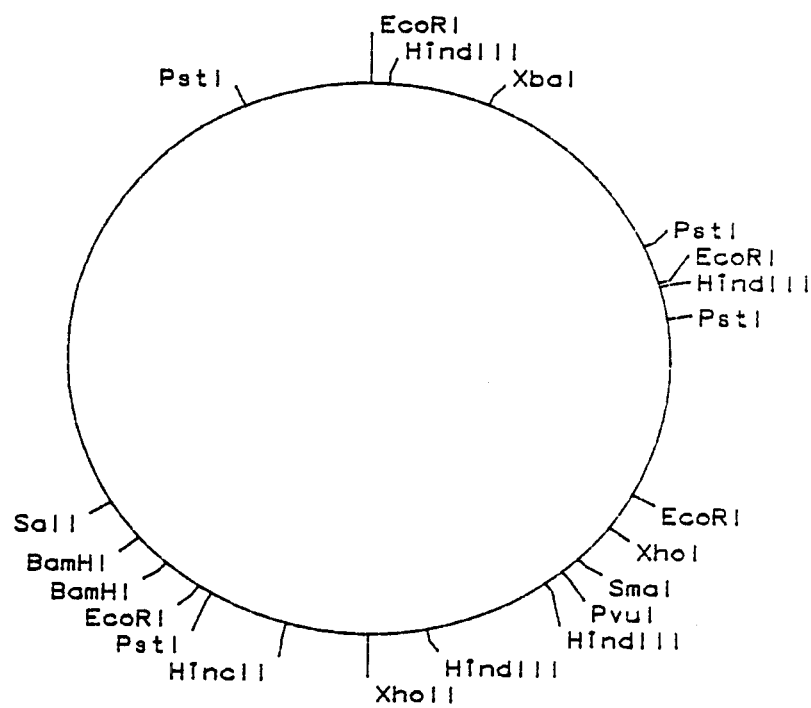
FIG. 7—Restriction Site Map of Plasmid pIT219.

About 2 μg of BamHI-linearized plasmid pIT213 and 2 μg of the ~230 BamHI fragment from plasmid were incubated together in buffer (20 mM Tris-HCl, pH 7.6, 10 mM MgCl$_2$, 0.5 mM ATP and 10 mM dithiothreitol) with 1000 (New England Biolabs) units of T4 ligase at 15° C. for two hours. The DNA was used to transform *E. coli* K12 RR1 (NRRL B-15210) and the desired plasmid pIT219 was isolated from the resulting ampicillin resistant *E. coli* transformants by the procedure of Example 1A. The structure of the plasmid was conventionally verified by restriction site mapping. A restriction site map of plasmid pIT219 is presented in FIG. 7 of the accompanying drawings.

4. Transformation of *Saccharomyces cerevisiae* with pIT219

The functioning of the *Saccharomyces cerevisiae* origin of replication and the functioning of the hybrid PGK/HPT gene in *S. cerevisiae* was demonstrated by the transformation of *S. cerevisiae* strains DBY-746 (ATCC 44773) and DBY-689 (commercially available from the Yeast Genetics Stock Center, Department of Biophysics and Medical Physics, University of California, Berkeley, California 94720) and by the observation of autonomous replication of plasmid pIT219 in the resulting hygromycin B resistant *S. cerevisiae* transformants. *Saccharomyces cerevisiae* protoplasts were prepared and transformed by the procedure described by Hinnen et al, 1978 Proc. Nat. Acad. Sci. USA 75:1929 with minor modifications. Accordingly, instead of adding the yeast to regeneration top agar as described by Hinnen et al., 1978,, the yeast was added to complete medium containing 1.2M sorbitol and 30 ml aliquots were added to each petri dish. To complement auxotrophs, the medium contained 0.67 percent yeast nitrogen base without amino acids (Difco), 2 percent dextrose, 3 percent agar, 1.2M sorbitol and other nutritional requirements at 20 μg/ml. For hygromycin B selections, the suspension medium contained 1 percent Bacto yeast extract, 2 percent Bacto peptone, 2 percent dextrose, 1.2M sorbitol, and 3 percent agar. After varying amounts of time, the plates were overlaid with the same solution containing 500 μg/ml hygromycin B.

Cells receiving pIT219 could be directly selected after transformation without first selecting for uracil prototrophy. The transformed cells were plated in 20 ml of YPD plus 1.2M sorbitol and 3 percent agar and incubated at 30° C. for varying lengths to time. They were then overlaid with 10 ml of the same medium containing 1.5 mg/ml hygromycin B and incubation was continued at 30° C. Although the recovery time required after transformation varied from experiment to experiment, satisfactory results could be achieved by adding the hygromycin B to one set of plates at four hours and to another set of plates at 20 hours after transformation. The requirement for recovery time may be related to the mechanism of action of hygromycin B. Adding the hygromycin B four hours after transformation killed the transformed cells as well as the untransformed cells in some experiments although in these cases adding the drug 20 hours after transformation did allow unambiguous selection of transformants. In other experiments, the background growth 20 hours after transformation was already too high to allow easy selection of transformants after adding the hygromycin B. Such variability could also be due to the extent of cell wall digestion by the zymolyase used in protoplasting.

C. Construction of Plasmid pIT221

1. Digestion of plasmid pIT220 with SalI restriction endonuclease

About 5 μg of plasmid pIT220 were incubated in SalI digestion buffer (10× buffer=1.5M NaCl, 0.06M Tris-HCl pH 7.5, 0.06M MgCl$_2$, 0.06M -mercaptoethanol) in 200 μl volume at 37° C. with 10 units of SalI restriction endonuclease until digestion was complete. The DNA was then purified as described in Example 6A(2).

2. Isolation of the ~3.3 kb SalI-XhoI fragment of plasmid pIT219

About 20 μg of pIT219 were incubated in 1× SalI digestion buffer in 200 μl volume at 37° C. with 10 units each of SalI and XhoI restriction enzymes until digestion was complete. The ~3.3 kb SalI-XhoI fragment was isolated and purified from a 7% polyacrylamide gel (60:1 acrylamide:bisacrylamide) as described in Example 6A(1).

3. Ligation of the ~3.3 kb SalI-XhoI fragment of plasmid pIT219 with SalI-cleaved plasmid pIT220

About 1 μg of SalI-cleaved pIT220 and 1 μg of the ~3.3 kb SalI-XhoI frament of plasmid pIT219 were ligated in substantial accordance with the teaching of this Example 6A(3). The desired recombinant plasmid pIT221 was isolated and purified in substantial accordance with the teaching of Example 1A. A restriction site map of plasmid pIT221 is presented in FIG. 1 of the accompanying drawings.

EXAMPLE 7

Genetic Transformation of Cephalosporium acremonium with Plasmid pIT221

A. *Cephalosporium acremonium* Strains

The preferred Cephalosporium strain for transformation is obtained from the American Type Culture Collection under the accession number ATCC 11550. Other restrictionless Cephalosporium strains or any commercial strains derived from ATCC 11550 by mutation/selection or genetic breeding for the purpose of improved production of cephalosporin C are also suitable for use.

B. Preparation of Inoculum for Cell Culture

To genetically transform *Cephalosporium acremonium* cells efficiently, it is necessary to remove the cell walls and form stable protoplasts. In the preparation of such protoplasts, it is highly advantageous to begin with a uniform inoculum. Otherwise, preparation of cells in culture is not reproducible and time is lost by attempts to prepare *C. acremonium* protoplasts from unsuitable or inadequate amounts of cells.

C. Preparation of Uniform Inoculum for Cell Culture

An ampoule of spores (approximatley $10^9$ conidia in 1.5 ml of preservation menstrum: 5% lactose, 10% glycerol, and 0.1% Tween 80) is taken from liquid nitrogen storage, thawed at room temperature and diluted in 5 ml of sterile saline. About 0.1 ml is used to inoculate each of approximately 50 slants containing 20 ml of Trypticase-Soy Agar (BBL) medium. Before inoculation, the medium is allowed to dry until surface moisture is no longer visible. Inoculated slants are incubated for about four days at 25° C. About 10 ml of preservation menstrum are added to the mycelial growth which covers the surface of the medium in each slant. The slants are vortexed to suspend the conidia and the conidial suspension from each slant is pooled and 10 ml aliquots frozen at $-80°$ C. The frozen conidial suspension slowly looses viability and should not be used after about three months of storage at $-80°$ C.

D. Growth of Cells for Preparation of Protoplasts

Approximately 106 ml of aqueous medium in a 500 ml shake flask is inoculated with cells from the 10 ml of frozen conidial suspension. Cells are obtained by centrifugation (10 min×2600 rpm), and then directly suspended in the aqueous culture medium*. Decantation of the supernatant is necessary prior to suspension because the lactose and glycerol adversely affect the growth of cells. The flask containing the suspended cells is placed on a gyratory water bath shaker and incubated 24 hours at 285 rpm with a 1 inch throw at 29°-30° C. It is important to observe the recommended temperature of 29°-30° C. in the culturing step to obtain cells suitable for preparing transformable protoplasts. However, lower temperatures of about 25° C. are also suitable. Those familiar with the art will recognize that the 29°-30° C. is different from the temperature (25° C.) preferred for culturing *Cephalosporium acremonium* for purposes of antibiotic production.

---

*Aqueous culture medium was prepared as follows: one hundred ml of solution A is dispensed into a 500 ml shake flask; the flask is covered with a commercial closure and is autoclaved at 121° C. for 20 minutes. Two ml of solution B and 4 ml of solution C are then added to solution A.
Solution A: Sucrose, 36 g/L; L-asparagine, 7.5 g/L; $KH_2PO_4$, 15 g/L; $K_2HPO_4$, 21 g/L; $Na_2SO_4$, .75 g/L, $MgSO_4.7H_2O$; .18 g/L; $CaCl_2$, .06 g/L; salts solution, 1 ml/L; natural pH. Salts solution: $Fe(NH_4)(SO_4)_2.6H_2O$, 15 g/L; $MnSO_4.4H_2O$, 3 g/l: $ZnSO_4.7H_2O$, 3 g/L; $CuSO_4.5H_2O$, 0.8 g/L).
Solution B: Glucose, 108 g/L (autoclaved at 121° C. 30 minutes)
Solution C: Sucrose, 25 g/L; corn steep liquor*, 12.5 ml; ammonium acetate, 5.5 g/L; $CaCO_3$, 5 g/L; pH adjusted to 6.5 with KOH; autoclaved at 121° C. for 20 minutes.
*4% nitrogen (w/v)

---

E. Preparation of Cephalosporium Protoplasts

Cells from a 24 hour culture are harvested by suction filtration (Whatman #1 paper in a Buchner funnel) and suspended in McIlvaine's Buffer, pH 7.1 (0.1M citric acid, 0.2M dibasic sodium phosphate) to which dithiothretiol has been added to a concentration of 0.01M. Sufficient buffer is added to attain a final cell concentration of 1 g (weighed after suction filtration) of cell mass per 20 ml of buffer. The cell suspension is placed on a gyratory water bath shaker in a 50 ml shake flask and incubated 90 minutes at 140 rpm with 1 inch throw at 29°-30° C. Dithiothreitol-treated cells are washed with water and then resuspended in enzyme solution (25 mg/ml of beta-glucuronidase-Sigma Chemical Comany, in McIlvaine's buffer, pH 6.35; supplemented with 0.8M NaCl and 0.02M $MgSO_4$). The final cell concentration is 1 g of treated cell mass per 10 ml of enzyme solution. The cell suspension is then placed on a gyratory water bath shaker and incubated for 3 hours at 120 rpm with 1 inch throw at 29°-30°° C. The suspension of protoplasts is diluted with 4 volumes of washing solution (0.8M NaCl and 0.02M $MgSO_4$) and then gravity filtered through two layers of paper toweling. The filtrate containing the protoplasts is centrifuged for 5 minutes at 2600 rpm at room temperature. The supernatant is decanted and the pellet of protoplasts suspended in 10 ml of washing solution. After the washing procedure is repeated twice, the washed protoplasts are resuspended in sufficient 0.08 NaCl to achieve a concentration of 2 to $3 \times 10^8$ protoplasts per ml (hemacytometer count).

F. Transformation Procedure

To a 1 ml suspension of Cephalosporium protoplasts (2 to $3 \times 10^8$ per ml) in 0.8M NaCl solution, 0.005 ml of freshly distilled DMSO and $CaCl_2$ to a final concentration of 80 mM are added followed by addition of about 1 to 20 micrograms of plasmid pIT221 DNA. Next, Polyethylene Glycol 4000 (Baker, >20% w/v in water) is added to achieve a mixture with a volume of 10 ml. The mixture is incubated for 10 minutes at room temperature and then centrifuged at 700 rpm for 5 minutes followed by 2500 rpm for 10 minutes. The pellet of protoplasts is suspended in 1 ml of 0.08M NaCl. Aliquots (0.1 ml) are delivered to the surface of Trypticase-Soy Agar medium (BBL) that has been enriched with 10.8% sucrose to osmotically stabilize the protoplasts. After the petri plates are incubated at 15° C. for 24 hours, 4 ml of liquified agar (0.41% w/v, at 42° C.) containing 0.8M sodium chloride and sufficient hygromycin to achieve a final concentration of 100 μg/ml are added to each petri dish. After the overlay has solidified, the petri plates are then incubated at 25° C. in a humidified chamber. Although transformant colonies of sufficient size to subculture are present 12 days after transformation, slower growing transformants may take as long as 60 days. Abortive transformants are easily distinguished from stable transformants because abortants fail to grow upon subculture to fresh selective medium.

EXAMPLE 8

Southern Hybridization of ($^{32}$P)pBR322 to High Molecular Weight DNA from Cephalosporium Transformant CPC-T1

Southern hybridization experiments provide unequivocal proof that hygromycin-resistant *Cephalosporium acremonium* transformants such as, for example, isolate CPC-T1, have been recovered from transformation experiments involving *C. acremonium* protoplasts and pIT221. In one experiment, about 2.2×10⁸ protoplasts were present in a 10 ml transformation mixture with 20 mcg of plasmid pIT221DNA. The entire transformation mixture, in 0.1 ml aliquots per petri dish, was delivered to selective medium and observed for 60 days. During this time three colonies grew. The largest of these colonies was designated CPC-T1 the smaller colonies were designated CPC-T2 and CPC-T3. A "dummy" pIT221 transformation mixture was also used. Otherwise the procedure was the same. A count of $6 \times 10^5$ colony forming units per ml of transformation mixture was obtained by plating aliquots of the "dummy" mixture on non-selective medium (no hygromycin present). No colonies grew on selective medium seeded with the "dummy" transformation mixture. A colony was selected from non-selective medium seeded with diluted (4 logs) "dummy" transformation mixture and was designated as a "control". A portion of colonies CPC-T1, -T2, and -T3 were preserved in liquid nitrogen. A portion of colony CPC-T1 was subcultured on non-selective medium and DNA was prepared from the CPC-T1 subculture and from the "control" subculture by the method of (Minuth et al., 1982. Equivalent amounts of DNA from isolate CPC-T1 and from the "control" isolate were electrophoresed in agarose gels. For comparison, purified DNA preparations from phage lambda, DNA from yeast strain DBY-746, and DNA from a YRp7-transformant of DBY-746 were also electrophoresed. Plasmid YRp7 (ATCC 37060) is a yeast/*E. coli* hybrid plasmid which is present in an autonomously replicating form in strain DBY-746/YRp7. The lambda DNA was digested with EcoRI/BamHI prior to electrophoresis. After electrophoresis and ethidium staining, the position of the EcoRI/BamHI DNA fragments were marked with their known sizes in kilobases (1.1 to 16.3). A Southern hybridization was performed on the agarose gel using ($^{32}$P)pBR322 as the DNA probe (nick-translation by the method of Rigby et al., 1977, J. Mol. Biol. 113:237). A band corresponding to the high molecular weight DNA from isolate CPC-T1 showed a clear and strong hybridization to the ($^{32}$P)pBR322 probe. In marked contrast, there was complete absence of hybridization to DNA from the "control", i.e., the untransformed recipient strain from the "dummy" transformation. Likewise, total DNA from yeast strain DBY-746 showed no hybridization to ($^{32}$P)pBR322 whereas total DNA from the YRp7-transformant of DBY-746 clearly showed bands of DNA which hybridize to ($^{32}$P)pBR322. These bands correspond to the ccc, linear, open circle and multimeric forms of the freely replicating plasmid YRp7, a plasmid known to contain pBR322 sequences as shown by Struhl et al., 1979, Proc. Natl. Acad. Sci. USA 76:1036.

The hybridization of the high molecular weight DNA of the hygromycin-resistant *Cephalosporium acremonium* isolate CPC-T1 to ($^{32}$P)pBR322 demonstrates that this isolate represents a transformant in which all or a portion of plasmid pIT221 has integrated into the Cephalosporium genome. No hybridization bands corresponding to a ccc, linear or open circle form of plasmid pIT221 were observed in the DNA from CPC-T1.

In separate experiments, it was shown that the high molecular weight DNA of the hygromycin-resistant isolates CPC-T2 and CPC-T3 also hybridized to ($^{32}$P)pBR322. Again, the DNA from untransformed *C. acremonium* controls did not hybridize.

EXAMPLE 9

Southern Hybridization of Plasmid ($^{32}$P)pBR322 to Restricted Total DNA from Cephalosporium Transformant CPC-T1

*Cephalosporium acremonium* cells (from clone CPC-T1) acquired genotypic resistance to hygromycin following transformation by plasmid pIT221 DNA. Because plasmid pIT221 contains DNA from plasmid pBR322, the presence of ($^{32}$P)pBR322-hybridizing DNA in the total uncut DNA from these hygromycin-resistant cells constitutes unequivocal proof that cells of clone CPC-T1 contained pIT221 DNA. The absence of ($^{32}$P)pBR322-hybridizing DNA in the total DNA from the strain prior to transformation demonstrates that the acquisition of hygromycin-resistance was associated with the acquisition of plasmid pIT221. The migration in agarose gels exhibited by ($^{32}$P)pBR322-hybridizing DNAs in the total uncut DNA from CPC-T1 demonstrates that plasmid pIT221 had integrated into the high molecular weight p *C. acremonium* DNA. The absence of (=P)pBR322-hybridizing DNA of low molecular weight in the total DNA of the hygromycin-resistant cells demonstrates that plasmid pIT221 did not exist in autonomously replicating forms in the cells of clone CPC-T1. Multiple sequences in restricted total DNA from Cephalosporium transformant CPC-T1 that hybridize to (=P)pBR322 do not reflect partial DNA digestion.

Integration of plasmid pIT221 was also shown to occur at more than one site. Since KpnI does not cut plasmid pIT221, if pIT221 was inserted only once in the fungal genome of CPC-T1 then only a single ($^{32}$P)pBR322-hybridizing fragment would be produced by KpnI digestion of total CPC-TI DNA. The two ($^{32}$P)pBR322-hybridizing fragments produced by KpnI digestion of total CPC-T1 DNA demonstrate that at least two integrations of plasmid pIT221 into the fungal genome occurred; one into a region of *Cephalosporium acremonium* DNA bounded by KpnI sites far from the inserted plasmid pIT221 DNA and one inserted into a region of *C. acremonium* DNA bounded by KpnI sites located near the ends of the inserted DNA. The number of ($^{32}$P)pBR322-hybridizing DNA fragments observed in SacI and XbaI digests of total CPC-T1 DNA also suggests that several integrations of plasmid pIT221 occur in CPC-T1. For each single integration into the fungal genome, two ($^{32}$P)pBR322-hybridizing fragments would be predicted in the complete SacI or XbaI digests of total CPC-T1 DNA. Eight DNA fragments that hybridized to ($^{32}$P)pBR322 were actually produced by complete digstion with SacI and six were produced by complete digestion with XbaI. These results indicate that about four separate integrations of plasmid pIT221 have occurred.

EXAMPLE 10

Detection of Plasmid pIT221-borne Hygromycin Phosphotransferase Gene Sequences in Transformants of *Cephalosporium acremonium*

To further define the basis of the hygromycin resistance exhibited by Cephalosporium transformant CPC-T1, it was necessary to physically test for the presence of plasmid pIT221-borne hygromycin phosphotransferase (HPT) gene sequences. Plasmid pJC10 is a suitable probe for carrying out this physical test. Plasmid pJC10 contains all of the HPT gene sequences present in pIT221 and was derived by circularizing the large BglII fragment from the previously described plasmid pKC203. A suitable probe contains the HPT gene but not other DNA that would hybridize to the DNA of plasmid pIT221 or to the recipient Cephalosporium strain. Plasmid pIT221 contains five types of DNA: (1) pBR322 sequences, (2) the sequences of the ~1.8 kb PstI fragment from Cephalosporium mitochondrial DNA, (3) sequences of an inactive fragment of Tn(601), (4) two *Saccharomyces cerevisiae* sequences: one on an ~275 kb BamHI fragment of yeast DNA that includes the PKG activating sequence and the second on a ~40 bp sequence that has no known function, and (5) sequences of a truncated form of the HPT gene from plasmid pKC203. The location of these DNAs is known from the construction of plasmid pIT221 as previously described. Plasmid (=P)pJC10 was used to probe samples of plasmid pIT221 DNA that were digested separately with PstI, BamHI, EcoRI, and HindIII restriction enzymes. These Southern hybridization experiments showed that only those fragments which contained the HPT gene sequences hybridized to the (=P)pJC10 probe.

EXAMPLE 11

Southern Hybridization of Plasmid (=P)pJC10 to the High Molecular Weight DNA of Cephalosporium Transformant CPC-T1

Uncut total DNA from untransformed Cephalosporium and uncut total DNA from plasmid pIT221-transformed Cephalosporium isolate CPC-T1 were electrophoresed on agarose gels. The DNA from the samples was probed with (=P)pJC10 using the Southern technique. The results demonstrate that (=P)pJC10 hybridizes to the high molecular weight DNA of Cephalosporium transformant CPC-T1. No bands corresponding to a autonomously replicating plasid were found. The inability of plasmid (=P)pJC10 to hybridize to DNA from untransformed Cephalosporium shows that CPC-T1 contains genomically integrated pIT221-borne HPT gene sequences. The same results were obtained with total uncut DNA from Cephalosporium transformants CPC-T2 and CPC-T3 in a separate Southern hybridization experiment using the same probe.

EXAMPLE 12

Hygromycin Resistance in Transformant CPC-T1 after Approximately 25 Generations of Growth in Non-selective Media To obtain a qualitative measure of the stability of *Cephalosporium acremonium-*/pIT221, a 0.5 cm portion of a CPC-T1 colony was removed from selective agar medium (contains 100 micrograms per milliliter hygromycin) and grown to a diameter of 14 cm on non-selective medium. The cells from the non-selective medium were removed, suspended in saline, homogenized, diluted and then plated on selective and non-selective media. Table II shows that the number of colony forming units was substantially the same on both selective and non-selective medium.

TABLE II

Stability of Cephalosporium Transformant CPC-T1 After Approximately 25 Generations of Growth on Non-selective Medium

| Trial No. | Percent of Cells Resistant |
| --- | --- |
| #1 | 100% |
| #2 | 94% |

Procedure:

A 0.5 cm patch of *Cephalosporium acremonium*/pIT221 cells growing on Trypticase-Soy agar medium (BBL) supplemented with 10.3 g of sucrose and 100 μg/ml of hygromycin B was transferred to Trypticase-Soy-Sucrose agar medium without hygromycin B. When the colony was 14 cm in diameter, the growth was removed from the non-selective medium, suspended in saline, homogenized to an even suspension, diluted in saline, and plated on Trypticase-Soy-Sucrose agar medium and also on the same medium supplemented with 100 μg/ml of hygromycin B. Results: experiment #1: CFU on non-selective medium=21; CFU on selective medium=22; experiment #2: CFU on non-selective=213; CFU on selective=201. The stability of the hygromycin-resistant phenotype of Cephalosporium transformant CPC-T1 is consistent with the physical proof of the presence of HPT gene sequences in the high molecular weight DNA of Cephalosporium transformants.

In a second experiment, an aliquot from a 48 hour vegetative culture of CPC-T1 was used to inoculate a medium capable of supporting cephalosporin C synthesis. After a 96 hour fermentation, aliquots of whole broth were analyzed for (1) antibiotics penicillin N and cephalosporin C; (2) the presence of viable cells; and (3) the presence of viable, hygromycin resistant cells. The number measured for viable CPC-T1 cells (grown on non-selective agar, i.e, no hygromycin present) was, by statistical analysis, substantially the same as that measured for viable, hygromycin-resistant CPC-T1 cells (grown on selective agar, i.e., hygromycin present). All untransformed Cephalosporium cells delivered to selective medium (100 μg/ml hygromycin B) failed to grow. Both the CPC-T1 transformant and its parent produced β-lactam antibiotics in the fermentation culture. On a cell weight basis, the amounts of antibiotic were approximately equivalent, although the growth rate and total cell mass of CPC-T1 was slightly lower than the untransformed parent. Those data illustrate that the plasmid pIT221-*C. acremonium* transformants are sufficiently stable for commercial use in the fermentation production of cephem antibiotics without the addition of hygromycin B as a selective agent.

EXAMPLE 13

Construction of Plasmid pPS6

A. Isolation of a Ribosomal DNA Sequence from *Cephalosporium acremonium*

1. Construction of a genomic library

The desired library was conventionally constructed from *Cephalosporium acremonium* (any *C. acremonium* strain, particularly ATCC 11550 and ATCC 14553 is acceptable) in substantial accordance with the method of Rimm et al., 1980, Gene 12:301. In addition, useful procedures for library construction are also disclosed in Maniatis et al., 1982. Bacteriophage Charon 28 and the host bacterial strain *E. coli* K12 Q359 were used to construct the library. Bacteriophage Charon 28 is commercially available from Bethesda Research Laboratory, Gaithersburg, Maryland while *E. coli* K12 Q359 has been deposited and made part of the permanent stock culture collection of the Regional Research Laboratory, Peoria, Illinois. The strain can be obtained under the accession number NRRL B-1589.

Total DNA from *Cephalosporium acremonium* was isolated in substantial accordance with the teaching of Example 5B. The DNA was partially digested with MboI restriction enzyme in substantial accordance with the teaching of Example 5C(2) except that MboI restric-DNA fragments were size fractionated on sucrose gradients. Fragments of ~15-20 kb were selected and used in the construction of the library.

The DNA from bacteriophage Charon 28 was digested to completion with BamHI restriction enzyme in substantial accordance with the teaching of Example 6B(1). Three fragments from the Charon 28 DNA were produced; a right arm, a middle ~7 kb "stuffer" fragment and a left arm. The middle ~7 kb "stuffer" fragment was removed by sucrose gradient fractionation and then the ~15-20 kb *Cephalosporium acremonium* DNA fragments were ligated to the left and right arms of the bacteriophage Charon 28 DNA in substantial accordance with the teaching of Example 6A(3). The ligated material was used in an in vitro packaging reaction. Materials required and kits for carrying out in vitro packaging are commercially available, for example, from Pro-mega Biotech, Madison, Wisconsin or other well known firms. The resultant bacteriophage particles were used to conventionally infect *E. coli* K12 Q359 and the resultant plaques were screened for the desired DNA sequences by the plaque hybidization technique described in Maniatis et al., 1982.

---

*Reaction mix for MboI restriction enzyme can be prepared with the following composition.
  100 mM NaCl
  50 mM Tris-HCl, pH 7.5
  10 mM MgCl$_2$
  1 mM Dithiothreitol

---

2. Screening of the genomic library for ribosomal DNA

This procedure is best carried out by use of a radioactive probe that contains a portion of the gene being sought or a closely related sequence. Plasmid pY1rA12 contains the yeast ribosomal RNA coding sequences for the 5.8, 18 and 25S ribosomal RNA genes and is preferred for screening. The plasmid has been deposited and made part of the permanent collections of the Northern Regional Research Laboratory and can be obtained under the accession number NRRL B-15888. Plasmid pY1rA12 was labeled by nick.translation with $^{32}$P-dCTP in substantial accordance with the method of Rigby et al., 1977, J. Mol. Biol. 113:237. A plaque which hybridized with labeled plasmid pY1rA12 DNA was purified and the DNA extracted from the bacteriophage as described in Maniatis et al., 1982. Restriction analysis and Southern hybidization analysis revealed that an ~3.7 kb XmaI fragment hybridized with plasmid pY1-rA12. The ~3.7 kb fragment was then isolated by electroelution onto DEAE cellulose paper, in substantial accordance with the teaching of Example 5C(1), and constituted the desired *Cephalosporium acremonium* ribosomal DNA-containing sequence.

B. XmaI Digestion of Plasmid pIT221

The desired digestion was carried out in substantial accordance with the procedure of Example 6A except that XmaI restriction enzyme and reaction buffer*, than PstI restriction enzyme and reaction buffer, were used. An ~274 bp and an ~8 kb fragment were produced and constituted the desired plasmid pIT221 digest.

---

*Reaction buffer for XmaI restriction enzyme can be prepared with the following composition:
  10 mM Tris-HCl, pH 7.5
  10 mM MgCl$_2$
  1 mM Dithiothreitol

---

C. Ligation and Final Construction of *E. coli* K12 C600/pPS6

Figure 8:
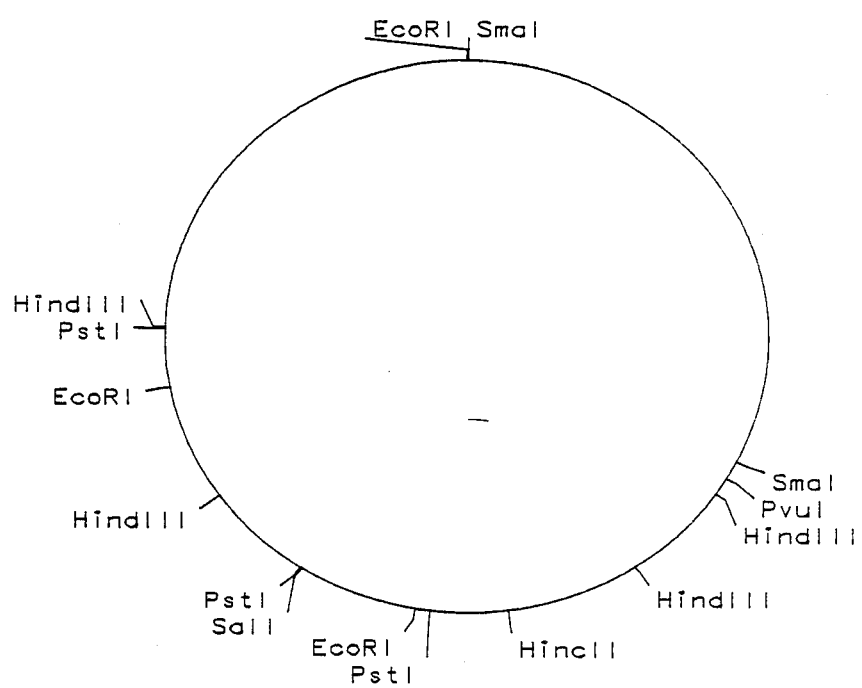
FIG. 8—Restriction Site Map of Plasmid pPS6.

About 0.125 μg of the ~3.7 kb XmaI fragment were mixed with about 0.1 μg of the plasmid pIT221 XmaI digest. The fragments were ligated in substantial accordance with the teaching of Example 5C(3). The resulting plasmid, designated as plasmid pPS6, was used to transform *E. coli* K12 C600 to ampicillin resistance in substantial accordance with the method of Mandel and Higa, 1970. Plasmid DNA was isolated from a purified transformant and analyzed by restriction enzyme analysis. A restriction site map of plasmid pPS6 is presented in FIG. 8 of the accompanying drawings.

EXAMPLE 14

Construction of *Cephalosporium acremonium*/pPS6

The desired construction was made in substantial accordance with the teaching of Example 7 except that plasmid pPS6, rather than plasmid pIT221, was used.

EXAMPLE 15

Construction of Plasmids pETS702 and pPLS221

A. PstI Digestion of Plasmid pIJ702

The desired digestion of plasmid pIJ702 (ATCC 39155) was carried out in substantial accordance with the teaching of Example 5C(2) except that a complete, rather than a partial, digestion was carried out.

B. Partial Digestion of Plasmid pIT221

The desired partial digestion was carried out in substantial accordance with the teaching of Example 5C(2) except that plasmid pIT221, rather than plasmid pRB12, was used.

C. Ligation and Final Construction of E. coli K12 C600/pETS702 and E. coli K12 C600/pPLS221

The desired ligation of the DNA digests of A and B above was carried out in substantial accordance with the teaching of Example 5C(3). The resultant plasmids, designated as plasmids pETS702 and pPLS221, are used to transform E. coli K12 C600 to ampicillin resistance in substantial accordance with the procedure of Mandel and Higa, 1970. Two ~13 kb plasmids result from the above ligation because the plasmid pIJ702 DNA can be ligated at the '5 o'clock' or '8 o'clock' PstI restriction sites of plasmid pIT221 (see FIG. 1). Ligation at the 5 o'clock site results in plasmid pETS702 and ligation at the 8 o'clock site results in plasmid pPLS221. The orientation of the pIJ702 fragment in both plasmids is such that the KpnI site is closest to the SalI site of the plasmid pIT221 DNA. The plasmids are conventionally isolated from the E. coli K12 C600 transformants and then identified by restriction enzyme analysis.

EXAMPLE 16

Construction of Streptomyces lividans/pPLS221

The desired construction is made in substantial accordance with the teaching of U.S. Pat. No. 4,468,462 (especially Example 9) except that Streptomyces lividans, rather than S. ambofaciens, is used.

EXAMPLE 17

Construction of Cephalosporium acremonium/pPLS221

The desired construction is made in substantial accordance with the teaching of Example 7 except that plasmid pPLS221, rather than plasmid pIT221, is used.

We claim:

1. A method for transforming a Cephalosporium host cell which comprises:
   (1) introducing a recombinant DNA cloning vector into a Cephalosporium host cell, said vector comprising
      (a) a *Saccharomyces cerevisiae* transcriptional and translational activating sequence positioned for expression of a sequence that codes for hygromycin B phosphotransferase and
      (b) a sequence that codes for hygromycin B phosphotransferase, subject to the limitation that the sequence of (a) is positioned for the expression of the sequence of (b), and
   (2) growing said host cell under selective conditions suitable for maintaining DNA comprising said vector in said host cell.

2. The method of claim 1 wherein the recombinant DNA cloning vector is a plasmid.

3. The method of claim 2 wherein the plasmid integrates into the genome of said host cell.

4. The method of claim 2 wherein the plasmid further comprises an E. coli origin of replication and a sequence that codes for a selectable phenotype in E. coli.

5. The method of claim 2 wherein the plasmid further comprises a Cephalosporium ribosomal DNA sequence.

6. The method of claim 2 wherein the plasmid further comprises a transcriptional and translational activating sequence positioned for expression of a sequence that codes for a functional polypeptide in Cephalosporium.

7. The method of claim 4 wherein the plasmid further comprises a Cephalosporium ribosomal DNA sequence.

8. The method of claim 4 wherein the plasmid further comprises a Streptomyces origin of replication and a sequence that codes for a selectable phenotype in Streptomyces.

9. The method of claim 8 wherein the plasmid further comprises a Cephalosporium ribosomal DNA sequence.

10. The method of claim 9 wherein the plasmid further comprises a transcriptional and translational activating sequence positioned for expression of a sequence that codes for a functional polypeptide in Cephalosporium.

11. The method of claim 2 wherein the *Saccharomyces cerevisiae* transcriptional and translational activating sequence is the phosphoglycerate kinase gene transcriptional and translational activating sequence.

12. The method of claim 2 wherein the sequence that codes for hygromycin B phosphotransferase is

```
                                                              Rm
                                                              |
                                                              R¹m
R²n    CCT  GAA  CTC  ACC  GCG  ACG  TCT  GTC  GAG  AAG  TTT  CTG
|      |||  |||  |||  |||  |||  |||  |||  |||  |||  |||  |||  |||
R³n    GGA  CTT  GAG  TGG  CGC  TGC  AGA  CAG  CTC  TTC  AAA  GAC

ATC  GAA  AAG  TTC  GAC  AGC  GTC  TCC  GAC  CTG  ATG  CAG  CTC
       |||  |||  |||  |||  |||  |||  |||  |||  |||  |||  |||  |||  |||
       TAG  CTT  TTC  AAG  CTG  TCG  CAG  AGG  CTG  GAC  TAC  GTC  GAG

TCG  GAG  GGC  GAA  GAA  TCT  CGT  GCT  TTC  AGC  TTC  GAT  GTA
       |||  |||  |||  |||  |||  |||  |||  |||  |||  |||  |||  |||  |||
       AGC  CTC  CCG  CTT  CTT  AGA  GCA  CGA  AAG  TCG  AAG  CTA  CAT
```

-continued

```
GGA  GGG  CGT  GGA  TAT  GTC  CTG  CGG  GTA  AAT  AGC  TGC  GCC
|||  |||  |||  |||  |||  |||  |||  |||  |||  |||  |||  |||  |||
CCT  CCC  GCA  CCT  ATA  CAG  GAC  GCC  CAT  TTA  TCG  ACG  CGG

GAT  GGT  TTC  TAC  AAA  GAT  CGT  TAT  GTT  TAT  CGG  CAC  TTT
|||  |||  |||  |||  |||  |||  |||  |||  |||  |||  |||  |||  |||
CTA  CCA  AAG  ATG  TTT  CTA  GCA  ATA  CAA  ATA  GCC  GTG  AAA

GCA  TCG  GCC  GCG  CTC  CCG  ATT  CCG  GAA  GTG  CTT  GAC  ATT
|||  |||  |||  |||  |||  |||  |||  |||  |||  |||  |||  |||  |||
CGT  AGC  CGG  CGC  GAG  GGC  TAA  GGC  CTT  CAC  GAA  CTG  TAA

GGG  GAA  TTC  AGC  GAG  AGC  CTG  ACC  TAT  TGC  ATC  TCC  CGC
|||  |||  |||  |||  |||  |||  |||  |||  |||  |||  |||  |||  |||
CCC  CTT  AAG  TCG  CTC  TCG  GAC  TGG  ATA  ACG  TAG  AGG  GCG

CGT  GCA  CAG  GGT  GTC  ACG  TTG  CAA  GAC  CTG  CCT  GAA  ACC
|||  |||  |||  |||  |||  |||  |||  |||  |||  |||  |||  |||  |||
GCA  CGT  GTC  CCA  CAG  TGC  AAC  GTT  CTG  GAC  GGA  CTT  TGG

GAA  CTG  CCC  GCT  GTT  CTG  CAG  CCG  GTC  GCG  GAG  GCC  ATG
|||  |||  |||  |||  |||  |||  |||  |||  |||  |||  |||  |||  |||
CTT  GAC  GGG  CGA  CAA  GAC  GTC  GGC  CAG  CGC  CTC  CGG  TAC

GAT  GCG  ATC  GCT  GCG  GCC  GAT  CTT  AGC  CAG  ACG  AGC  GGG
|||  |||  |||  |||  |||  |||  |||  |||  |||  |||  |||  |||  |||
CTA  CGC  TAG  CGA  CGC  CGG  CTA  GAA  TCG  GTC  TGC  TCG  CCC

TTC  GGC  CCA  TTC  GGA  CCG  CAA  GGA  ATC  GGT  CAA  TAC  ACT
|||  |||  |||  |||  |||  |||  |||  |||  |||  |||  |||  |||  |||
AAG  CCG  GGT  AAG  CCT  GGC  GTT  CCT  TAG  CCA  GTT  ATG  TGA

ACA  TGG  CGT  GAT  TTC  ATA  TGC  GCG  ATT  GCT  GAT  CCC  CAT
|||  |||  |||  |||  |||  |||  |||  |||  |||  |||  |||  |||  |||
TGT  ACC  GCA  CTA  AAG  TAT  ACG  CGC  TAA  CGA  CTA  GGG  GTA

GTG  TAT  CAC  TGG  CAA  ACT  GTG  ATG  GAC  GAC  ACC  GTC  AGT
|||  |||  |||  |||  |||  |||  |||  |||  |||  |||  |||  |||  |||
CAC  ATA  GTG  ACC  GTT  TGA  CAC  TAC  CTG  CTG  TGG  CAG  TCA

GCG  TCC  GTC  GCG  CAG  GCT  CTC  GAT  GAG  CTG  ATG  CTT  TGG
|||  |||  |||  |||  |||  |||  |||  |||  |||  |||  |||  |||  |||
CGC  AGG  CAG  CGC  GTC  CGA  GAG  CTA  CTC  GAC  TAC  GAA  ACC

GCC  GAG  GAC  TGC  CCC  GAA  GTC  CGG  CAC  CTC  GTG  CAC  GCG
|||  |||  |||  |||  |||  |||  |||  |||  |||  |||  |||  |||  |||
CGG  CTC  CTG  ACG  GGG  CTT  CAG  GCC  GTG  GAG  CAC  GTG  CGC

GAT  TTC  GGC  TCC  AAC  AAT  GTC  CTG  ACG  GAC  AAT  GGC  CGC
|||  |||  |||  |||  |||  |||  |||  |||  |||  |||  |||  |||  |||
CTA  AAG  CCG  AGG  TTG  TTA  CAG  GAC  TGC  CTG  TTA  CCG  GCG

ATA  ACA  GCG  GTC  ATT  GAC  TGG  AGC  GAG  GCG  ATG  TTC  GGG
|||  |||  |||  |||  |||  |||  |||  |||  |||  |||  |||  |||  |||
TAT  TGT  CGC  CAG  TAA  CTG  ACC  TCG  CTC  CGC  TAC  AAG  CCC

GAT  TCC  CAA  TAC  GAG  GTC  GCC  AAC  ATC  TTC  TTC  TGG  AGG
|||  |||  |||  |||  |||  |||  |||  |||  |||  |||  |||  |||  |||
CTA  AGG  GTT  ATG  CTC  CAG  CGG  TTG  TAG  AAG  AAG  ACC  TCC

CCG  TGG  TTG  GCT  TGT  ATG  GAG  CAG  CAG  ACG  CGC  TAC  TTC
|||  |||  |||  |||  |||  |||  |||  |||  |||  |||  |||  |||  |||
GGC  ACC  AAC  CGA  ACA  TAC  CTC  GTC  GTC  TGC  GCG  ATG  AAG
```

```
GAT TTC GGC TCC AAC AAT GTC CTG ACG GAC AAT GGT CGC
||| ||| ||| ||| ||| ||| ||| ||| ||| ||| ||| ||| |||
CTA AAG CCG AGG TTG TTA CAG GAC TGC CTG TTA CCG GCG

ATA ACA GCG GTC ATT CAG RGG AGC CTC GCG ATG TTC GGG
||| ||| ||| ||| ||| ||| ||| ||| ||| ||| ||| ||| |||
TAT TGT CGC CAG TAA CTG ACC TCG GAG CGC TAC AAG CCC

GAT TCC CAA TAC GAG GTC GCC AAC ATC TTC TTC TGG AGG
||| ||| ||| ||| ||| ||| ||| ||| ||| ||| ||| ||| |||
CTA AGG GTT ATG CTC CAG CGG TTG TAG AAG AAG ACC TCC

CCG TGG TTG GCT TGT ATG GAG CAG CAG ACG CGC TAC TTC
||| ||| ||| ||| ||| ||| ||| ||| ||| ||| ||| ||| |||
GGC ACC AAC CGA ACA TAC CTC GTC GTC TGC GCG ATG AAG

GAG CGG AGG CAT CCG GAG CTT GCA GGA TCG CCG CGG CTC
||| ||| ||| ||| ||| ||| ||| ||| ||| ||| ||| ||| |||
CTC GCC TCC GTA GGC CTC GAA CGT CCT AGC GGC GCC GAG

CGG GCG TAT ATG CTC CGC ATT GGT CTT GAC CAA CTC TAT
||| ||| ||| ||| ||| ||| ||| ||| ||| ||| ||| ||| |||
GCC CGC ATA TAC GAG GCG TAA CCA GAA CTG GTT GAG ATA

CAG AGC TTG GTT GAC GGC AAT TTC GAT GAT GCA GCT TGG
||| ||| ||| ||| ||| ||| ||| ||| ||| ||| ||| ||| |||
GTC TCG AAC CAA CTG CCG TTA AAG CTA CTA CGT CGA ACC

GCG CAG GGT CGA TGC GAC GCA ATC GTC CGA TCC GGA GCC
||| ||| ||| ||| ||| ||| ||| ||| ||| ||| ||| ||| |||
CGC GTC CCA GCT ACG CTG CGT TAG CAG GCT AGG CCT CGG

GGG ACT GTC GGG CGT ACA CAA ATC GCC CGC AGA AGC GCG
||| ||| ||| ||| ||| ||| ||| ||| ||| ||| ||| ||| |||
CCC TGA CAG CCC GCA TGT GTT TAG CGG GCG TCT TCG CGC

GCC GTC TGG ACC GAT GGC TGT GTA GAA GTA CTC GCC GAT
||| ||| ||| ||| ||| ||| ||| ||| ||| ||| ||| ||| |||
CGG CAG ACC TGG CTA CCG ACA CAT CTT CAT GAG CGG CTA

AGT GGA AAC CGA CGC CCC AGC ACT CGT CCG AGG GCA AAG
||| ||| ||| ||| ||| ||| ||| ||| ||| ||| ||| ||| |||
TCA CCT TTG GCT GCG GGG TCG TGA GCA GGC TCC CGT TTC

GAA  R⁴
|||  |
CTT  R⁵
``` wherein

A is deoxyadenyl,
G is deoxyguanyl,
C is deoxycytidyl,
T is thymidyl,
R and R² are deoxyribonucleotide triplets that independently encode lysine,
R¹ and R³ are deoxyribonucleotide triplets wherein the nitrogenous bases are complementary to the respective and corresponding bases of R and R²,
m and n=0 or 1, subject to the limitation that when n=0, then m=0 and when m=1, then n=1,
R⁴ is a deoxyribonucleotide triplet that encodes a translational stop codon and
R⁵ is a deoxyribonucleotide triplet wherein the nitrogenous bases are complementary to the corresponding bases of R⁴.

13. The method of claim 12 wherein the *Saccharomyces cerevisiae* transcriptional and translational activating sequence is the phosphoglycerate kinase gene transcriptional and translational activating sequence.

14. The method of claim 13 wherein the plasmid further comprises an E. coli origin of replication and a sequence that codes for a selectable phenotype in *E. coli*.

15. The method of claim 13 wherein the plasmid further comprises a Cephalosporium ribosomal DNA sequence.

16. The method of claim 13 wherein the plasmid further comprises a Streptomyces origin of replication and a sequence that codes for a selectable phenotype in Streptomyces.

17. The method of claim 16 wherein the plasmid further comprises a Cephalosporium ribosomal DNA sequence.

18. The method of claim 17 wherein the plasmid further comprises a transcriptional and translational activating sequence positioned for expression of a sequence that codes for a functional polypeptide in Cephalosporium.

19. The method of claim 1 wherein said host cells are grown on a growth medium containing antibiotic hygromycin B.

20. The method of claim 19 wherein the concentration of hygromycin B is within the range of about 8 μg/ml to about 5 mg/ml.

21. The method of claim 20 wherein the hygromycin B concentration is 100 μg/ml.

22. The method of claim 19 wherein the recombinant DNA cloning vector is plasmid pIT221.

23. The method of claim 19 wherein the recombinant DNA cloning vector is plasmid pPS6.

24. The method of claim 19 wherein the recombinant DNA cloning vector is plasmid pETS702.

25. The method of claim 19 wherein the recombinant DNA cloning vector is plasmid pPLS221.

26. The method of claim 1 wherein said Cephalosporium host cell is *C. acremonium*.

27. The method of claim 1 wherein the host cell is *Cephalosporium acremonium*/pIT221.

28. The method of claim 19 wherein the host cell is *Cephalosporium acremonium*/pIT221.

29. The method of claim 1 wherein the host cell is *Cephalosporium acremonium*/pPS6.

30. A recombinant DNA cloning vector which is plasmid pPS5.

31. A recombinant DNA cloning vector which is selected from the group consisting of plasmids pIT221 and pPS6.

32. A recombinant DNA cloning vector selected from the group consisting of plasmids pIT220, pETS702 and pPLS221.

33. A transformed Cephalosporium host cell employed in the method of claim 1.

34. The host cell of claim 33 which is *Cephalosporium acremonium*.

35. The host cell of claim 34 which is *Cephalosporium acremonium*/pPS5.

36. The host cell of claim 34 which is selected from the group consisting of *Cephalosporium acremonium*/pIT221 and *Cephalosporium acremonium*/pPS6.

37. A host cell selected from the group consisting of *Streptomyces lividans*/pETS702, *Streptomyces lividans*/pPLS221, *E. coli* K12/pETS702, *E. coli* K12/pPLS221, *E. coli* K12 RR1/pIT221, *E. coli* K12 RR1/pPSI, *E. coli* K-12 RR1/pPS5 and *E. coli* K12 RR1/pPS6.

38. A Streptomyces host cell transformed with a plasmid employed in the method of claim 8.

39. A method for transforming a lower eukaryotic host cell which comprises introducing a recombinant DNA cloning vector into a lower eukaryotic host cell exclusive of yeast and growing said host cell under selective conditions suitable for maintaining DNA comprising said vector in said host cell wherein said vector is a vector employed in the method of claim 1.

40. The method of claim 39 wherein the host cell is Penicillium.

41. The method of claim 40 wherein the Penicillium is selected from the group consisting of *P. chrysogenum* and *P. notatum*.

42. The method of claim 39 wherein the host cell is selected from the group consisting of Aspergillus and Paecilomyces.

43. The method of claim I wherein the host cell is selected from the group consisting of *Cephalosporium salmyosynnematum*, *C. chrysogenum*, *C. purpurascens* and *C. curtipis*.

* * * * *

UNITED STATES PATENT AND TRADEMARK OFFICE
CERTIFICATE OF CORRECTION

PATENT NO. : 4,762,786

DATED : August 9, 1988

INVENTOR(S) : Jerry L. Chapman, Jr., Thomas D. Ingolia, et al.

It is certified that error appears in the above-identified patent and that said Letters Patent is hereby corrected as shown below:

Please delete a portion of the DNA sequence of Claim 12 which was duplicated during the printing of this patent. The last 312 nucleotides on page 41-42 are incorrectly repeated at the top of page 43-44. In other words, the last 4 rows of double-stranded DNA sequence at the bottom of page 41-42 is repeated as the first 4 rows of double-stranded DNA sequence on page 43-44. Please delete the first 4 rows of double-stranded DNA sequence from page 43-44 to correct this redundancy.

Signed and Sealed this

Twenty-second Day of January, 1991

Attest:

HARRY F. MANBECK, JR.

Attesting Officer

Commissioner of Patents and Trademarks